United States Patent
Yamada et al.

(10) Patent No.: US 11,420,928 B2
(45) Date of Patent: Aug. 23, 2022

(54) POLYMER PHOTOPOLYMERIZATION SENSITIZER

(71) Applicant: Kawasaki Kasei Chemicals Ltd., Kawasaki (JP)

(72) Inventors: Akihiko Yamada, Kawasaki (JP); Shuji Yokoyama, Kawasaki (JP); Shigeaki Numata, Kawasaki (JP); Tatsuki Takeuchi, Kawasaki (JP)

(73) Assignee: Kawasaki Kasei Chemicals Ltd., Kawasaki (JP)

( * ) Notice: Subject to any disclaimer, the term of this patent is extended or adjusted under 35 U.S.C. 154(b) by 38 days.

(21) Appl. No.: 16/609,824

(22) PCT Filed: May 15, 2018

(86) PCT No.: PCT/JP2018/018753
§ 371 (c)(1),
(2) Date: Oct. 31, 2019

(87) PCT Pub. No.: WO2018/212176
PCT Pub. Date: Nov. 22, 2018

(65) Prior Publication Data
US 2020/0062692 A1 Feb. 27, 2020

(30) Foreign Application Priority Data
May 17, 2017 (JP) .............................. JP2017-097915

(51) Int. Cl.
| | |
|---|---|
| C07C 69/72 | (2006.01) |
| C07C 43/20 | (2006.01) |
| C07C 43/23 | (2006.01) |
| C07C 69/716 | (2006.01) |
| C07C 271/52 | (2006.01) |
| C07C 271/56 | (2006.01) |
| C07C 271/58 | (2006.01) |
| C08F 220/30 | (2006.01) |
| C08G 59/06 | (2006.01) |
| C08G 63/197 | (2006.01) |

(52) U.S. Cl.
CPC ............. *C07C 69/72* (2013.01); *C07C 43/20* (2013.01); *C07C 43/23* (2013.01); *C07C 69/716* (2013.01); *C07C 271/52* (2013.01); *C07C 271/56* (2013.01); *C07C 271/58* (2013.01); *C08F 220/30* (2013.01); *C08G 59/063* (2013.01); *C08G 63/197* (2013.01); *C07C 2601/14* (2017.05); *C07C 2603/24* (2017.05); *C08F 220/301* (2020.02)

(58) Field of Classification Search
None
See application file for complete search history.

(56) References Cited

U.S. PATENT DOCUMENTS

| | | | | |
|---|---|---|---|---|
| 4,444,861 A | * | 4/1984 | Nogami ................. | G03G 5/102 430/58.05 |
| 4,463,162 A | * | 7/1984 | Nogami ............. | C08G 65/4006 528/125 |
| 5,840,452 A | * | 11/1998 | Kitagawa ............... | G03G 5/076 430/31 |
| 7,279,607 B2 | * | 10/2007 | Honda .................... | C07C 41/16 568/633 |
| 2018/0208689 A1 | * | 7/2018 | Numata .................... | C08F 2/48 |

FOREIGN PATENT DOCUMENTS

| | | | |
|---|---|---|---|
| CN | 1714065 A | | 12/2005 |
| CN | 105037587 A | * | 11/2015 |
| CN | 105037587 A | | 11/2015 |
| JP | 57-96010 A | | 6/1982 |
| JP | 57-96018 A | | 6/1982 |

(Continued)

OTHER PUBLICATIONS

CN-105037587-A, Nov. 2015, Derwent abstract (Year: 2015).*
JP-2015059188-A, English Abstarct (Year: 2015).*
International Search Report dated Aug. 14, 2018 in PCT/JP2018/018753 filed on May 15, 2018.
Bender, D. et al., "Reductive transformations, 14. Soluble polyesters derived from 9,10-anthracenediols (1)," Polymer Bulletin, 1989, vol. 22, pp. 137-141.

(Continued)

*Primary Examiner* — Satya B Sastri
(74) *Attorney, Agent, or Firm* — Oblon, McClelland, Maier & Neustadt, L.L.P.

(57) ABSTRACT

To provide a photopolymerization sensitizer which will not cause problems of dusting or coloring of a cured product by bleeding of additives such as the photopolymerization sensitizer on the surface e.g. by blooming at the time of photo-curing or during storage of the cured product, and which imparts a practically sufficient photo-curing rate.
An oligomer of a 9,10-bis(substituted oxy)anthracene compound having repeating units represented by the following formula (1):

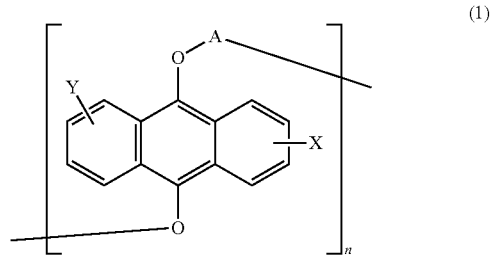

wherein n represents a repetition number and is from 2 to 50, each of X and Y which may be the same or different, is a hydrogen atom, a $C_{1-8}$ alkyl group or a halogen atom, and A is a bivalent substituent.

5 Claims, No Drawings

(56) References Cited

FOREIGN PATENT DOCUMENTS

| | | | |
|---|---|---|---|
| JP | 57-98523 A | 6/1982 | |
| JP | 60-179420 A | 9/1985 | |
| JP | 4-358157 A | 12/1992 | |
| JP | 5-249606 A | 9/1993 | |
| JP | 6-345614 A | 12/1994 | |
| JP | 7-62010 A | 3/1995 | |
| JP | 10-195117 A | 7/1998 | |
| JP | 11-279212 A | 10/1999 | |
| JP | 11-322900 A | 11/1999 | |
| JP | 2000-344704 A | 12/2000 | |
| JP | 2002-302507 A | 10/2002 | |
| JP | 2004-292766 A | 10/2004 | |
| JP | 2005-154748 A | 6/2005 | |
| JP | 2007-204438 A | 8/2007 | |
| JP | 2010-120853 A | 6/2010 | |
| JP | 2010-254585 A | 11/2010 | |
| JP | 2011-219666 A | 11/2011 | |
| JP | 2013-14674 A | 1/2013 | |
| JP | 2015-59188 | 3/2015 | |
| JP | 2015059188 A * | 3/2015 | ............ C07C 69/16 |
| JP | 2017-114849 A | 6/2017 | |
| KR | 10-2017-0000486 A | 1/2017 | |
| WO | WO 2007/126066 A1 | 11/2007 | |
| WO | WO-2017047599 A1 * | 3/2017 | ............ C08F 220/10 |

OTHER PUBLICATIONS

Chronakis, N. et al., "Macrocyclic Cyclo[n] malonates—Synthetic Aspects and Observation of Columnar Arrangements by X-ray Crystallography," European Journal of Organic Chemistry, 2006, No. 10, pp. 2296-2308, DOI: 10.1002/ejoc.200500921.

Castellan, A. et al., "Synthesis of new macrocyclic polyoxa[x.x] and [x](9,10)-anthracenophanes from 9,10-bistrimethylsiloxyanthracene," Tetrahedron Letters, 1983, vol. 24, No. 47, pp. 5215-5218.

Bouas-Laurent, H. et al., "Cation-Directed Photochemistry of an Anthraceno-Crown Ether," Journal of the American Chemical Society, 1986, vol. 108, No. 2, pp. 315-317.

Fages, F. et al., "Synthesis, Structural, Spectroscopic, and Alkali-Metal Cations Complexation Studies of a Bis-Anthracenediyl Macrotricyclic Ditopic Receptor," Journal of Organic Chemistry, 1994, vol. 59, No. 18, pp. 5264-5271.

Marquis, D. et al., "Photoresponsive Supramolecular Systems: Synthesis and Photophysical and Photochemical Study of Bis-(9,10-anthracenediyl) coronands AAOnOn", Journal of Organic Chemistry, 1995, vol. 60, No. 24, pp. 7984-7996.

Sinigersky, V. et al., "Synthesis and properties of anthracene containing polyethers," Macromolecular Chemistry and Physics, 2000, vol. 201, No. 11, pp. 1134-1140.

Diekers, M. et al., "$T_h$-Symmetrical Hexakisadducts of $C_{60}$ with a Densely Packed π-Donor Shell Can Act as Energy- or Electron-Transducing Systems," Chemistry European Journal, 2002, vol. 8, No. 4, pp. 979-991.

Schild, V. et al., "Tuning the Charge-Separated Lifetimes of Ruthenium(II)polypyridyl-Viologen Dyads and Ruthenium(II) polypyridyl-Viologen Triads by the Formation of Supramolecular Assemblies with Crown Ethers," Journal of Physical Chemistry A, 2002, vol. 106, No. 40, pp. 9149-9158.

Registry [online], US: American Chemical Society [retrieved on Jul. 12, 2018], Retrieved from: SIN, CAS RN 1020728-13-5; 782499-15-4; 677308-97-3; 435310-52-4; 371778-43-7; 197006-34-1; 174761-54-7; 129573-07-5; 128952-42-1; 128321-35-7; 126425-19-2; 89857-34-1; 89777-12-8; 89777-11-7 (total 15 pages).

4th Edition: Experimental Chemistry Lecture 22—Organic Synthesis IV, Edition of the Chemical Society of Japan, Maruzen Inc, 1992, pp. 43-47 and pp. 50-53 (total 10 pages).

* cited by examiner

POLYMER PHOTOPOLYMERIZATION SENSITIZER

TECHNICAL FIELD

The present invention relates to an oligomer of a 9,10-bis(substituted oxy)anthracene compound, its production method, and a photopolymerization sensitizer containing an oligomer of a 9,10-bis(substituted oxy)anthracene compound.

BACKGROUND ART

A photo-curing resin polymerizable by active energy rays such as ultraviolet rays or visible rays, which is quickly cured and can thereby remarkably reduce the amount of an organic solvent used as compared with a thermosetting resin, is superior in that the working environment can be improved and the environmental burden can be reduced. A conventional photo-curing resin by itself lacks polymerization initiation function and usually requires a photopolymerization initiator so as to be cured. The photopolymerization initiator may, for example, be an alkylphenone polymerization initiator such as hydroxyacetophenone or benzophenone, an acylphosphine oxide photopolymerization initiator or an onium salt (Patent Documents 1, 2 and 3). If an onium salt initiator is used among such photopolymerization initiators, an onium salt has light absorption in the vicinity of from 225 nm to 350 nm and has no absorption at a wavelength of 350 nm or longer, and accordingly if a long wavelength lamp at a wavelength of at least 350 nm is used as a light source, the photo-curing reaction hardly proceeds, and it is common to add a photopolymerization sensitizer. As a photopolymerization sensitizer, anthracene and thioxanthone compounds are known, and particularly an anthracene compound is used in many cases in view of the color, etc. (Patent Document 4).

As the anthracene photopolymerization sensitizer, a 9,10-dialkoxyanthracene compound is used. For example, for a iodonium salt which is a photopolymerization initiator in photopolymerization, as the photopolymerization sensitizer, a 9,10-dialkoxyanthracene compound such as 9,10-dibutoxyanthracene or 9,10-diethoxyanthracene has been used (Patent Documents 5, 6, 7 and 8).

However, it is known that additives such as the photopolymerization sensitizer bleed on the surface e.g. by blooming at the time of photo-curing or during storage of the cured product, thus leading to problems of dusting or coloring of the cured product. For example, in a case where the above photopolymerization sensitizer is used as a component of a photo-adhesive to bond films, the photopolymerization sensitizer may migrate to the upper film, thus leading to a problem of dusting or coloring of the sensitizer on the upper film.

As a method to suppress migration property, a method has been known to make the photopolymerization sensitizer have a high molecular weight thereby to lower mobility of the molecules. For example, in Patent Document 9, a photopolymerization sensitizer and a polyester resin are chemically bonded thereby to reduce the amount of the photopolymerization sensitizer having high migration property used, thereby to reduce migration, elution and volatilization of the photopolymerization sensitizer after the curing reaction.

However, in the method in Patent Document 9 in which the photopolymerization sensitizer is chemically bonded to the polyester resin as a pendant, the number of reactive groups (groups having a photopolymerization sensitizing effect) per unit molecular weight reduces, whereby the curing performance is deteriorated, and the problems have not been dissolved yet.

PRIOR ART DOCUMENTS

Patent Documents

Patent Document 1: JP-A-H06-345614
Patent Document 2: JP-A-H07-062010
Patent Document 3: JP-A-H05-249606
Patent Document 4: JP-A-H10-195117
Patent Document 5: JP-A-2002-302507
Patent Document 6: JP-A-H11-279212
Patent Document 7: JP-A-2000-344704
Patent Document 8: WO2007/126066
Patent Document 9: JP-A-2005-154748

DISCLOSURE OF INVENTION

Technical Problem

Therefore, development of a photopolymerization sensitizer which will not cause problems of dusting or coloring of a cured product by bleeding of additives such as the photopolymerization sensitizer on the surface e.g. by blooming at the time of photo-curing or during storage of the cured product, and which imparts a practically sufficient photo-curing rate, has been desired.

Solution to Problem

The present inventors have conducted extensive studies on the structure and physical properties of an anthracene compound and as a result, found the following and accomplished the present invention. That is, the oligomer of a 9,10-bis(substituted oxy)anthracene compound of the present invention has the same skeleton as a 9,10-dialkoxyanthracene or a 9,10-diacyloxyanthracene, has a number of the anthracene skeleton having a photopolymerization sensitizing effect per unit molecular weight, and has an excellent effect as a photopolymerization sensitizer in photocationic polymerization and photoradical polymerization. In addition, since the oligomer of a 9,10-bis(substituted oxy)anthracene compound of the present invention has a high molecular weight, even in a case where a film is covered on a photopolymerizable composition containing the compound as a photopolymerization sensitizer, migration or the like hardly occurs.

That is, the present invention has the following constructions.

(1) An oligomer of a 9,10-bis(substituted oxy)anthracene compound having repeating units represented by the following formula (1):

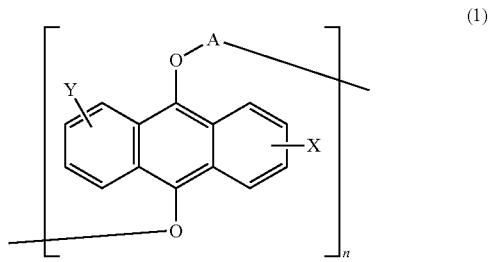

wherein n represents a repetition number and is from 2 to 50, each of X and Y which may be the same or different, is a hydrogen atom, a $C_{1-8}$ alkyl group or a halogen atom, and A is a bivalent substituent.

(2) An oligomer of a 9,10-bis(substituted oxy)anthracene compound having repeating units represented by the following formula (2):

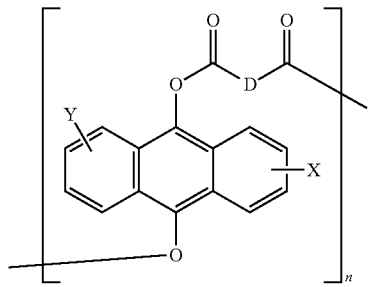

wherein n represents a repetition number and is from 2 to 50, each of X and Y which may be the same or different, is a hydrogen atom, a $C_{1-8}$ alkyl group or a halogen atom, D is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(3) An oligomer of a 9,10-bis(substituted oxy)anthracene compound having repeating units represented by the following formula (3):

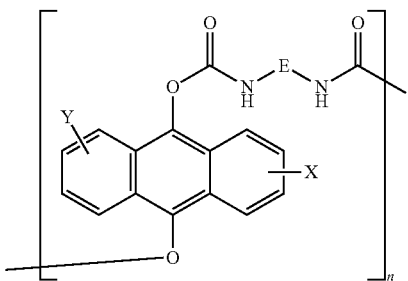

wherein n represents a repetition number and is from 2 to 50, each of X and Y which may be the same or different, is a hydrogen atom, a $C_{1-8}$ alkyl group or a halogen atom, E is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(4) An oligomer of a 9,10-bis(substituted oxy)anthracene compound having repeating units represented by the following formula (4):

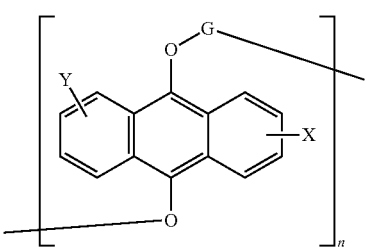

wherein n represents a repetition number and is from 2 to 50, each of X and Y which may be the same or different, is a hydrogen atom, a $C_{1-8}$ alkyl group or a halogen atom, G is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(5) An oligomer of a 9,10-bis(substituted oxy)anthracene compound having repeating units represented by the following formula (5):

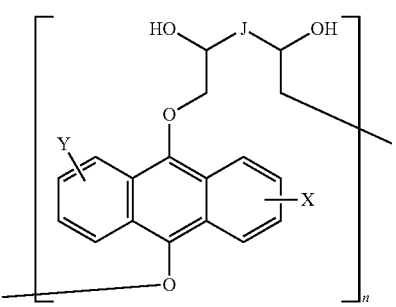

wherein n represents a repetition number and is from 2 to 50, each of X and Y which may be the same or different, is a hydrogen atom, a $C_{1-8}$ alkyl group or a halogen atom, J is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(6) A method for producing an oligomer of a 9,10-bis (substituted oxy)anthracene compound having repeating units represented by the formula (2), which comprises reacting a 9,10-dihydroxyanthracene compound represented by the following formula (6) and a dibasic acid, a dibasic acid halide or a dibasic acid ester:

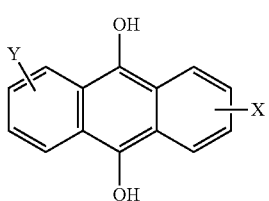

(6)

wherein each of X and Y which may be the same or different, is a hydrogen atom, a $C_{1-8}$ alkyl group or a halogen atom;

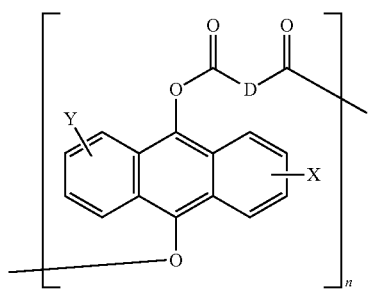

(2)

wherein n represents a repetition number and is from 2 to 50, each of X and Y which may be the same or different, is a hydrogen atom, a $C_{1-8}$ alkyl group or a halogen atom, D is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(7) A method for producing an oligomer of a 9,10-bis (substituted oxy)anthracene compound having repeating units represented by the formula (3), which comprises reacting a 9,10-dihydroxyanthracene compound represented by the following formula (6) and a diisocyanate compound:

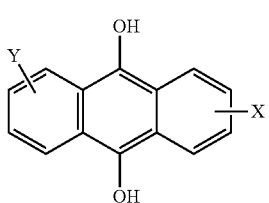

(6)

wherein each of X and Y which may be the same or different, is a hydrogen atom, a $C_{1-8}$ alkyl group or a halogen atom;

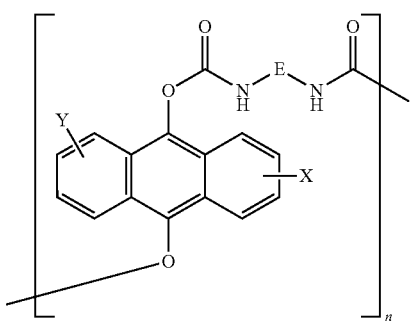

(3)

wherein n represents a repetition number and is from 2 to 50, each of X and Y which may be the same or different, is a hydrogen atom, a $C_{1-8}$ alkyl group or a halogen atom, E is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(8) A method for producing an oligomer of a 9,10-bis (substituted oxy)anthracene compound having repeating units represented by the formula (4), which comprises reacting a 9,10-dihydroxyanthracene compound represented by the following formula (6) and a dihalogen compound or a diol compound:

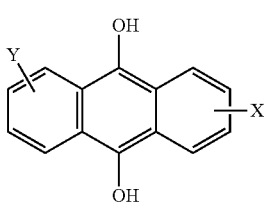

(6)

wherein each of X and Y which may be the same or different, is a hydrogen atom, a $C_{1-8}$ alkyl group or a halogen atom;

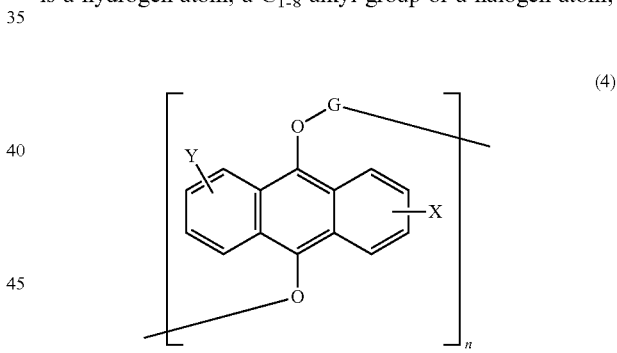

(4)

wherein n represents a repetition number and is from 2 to 50, each of X and Y which may be the same or different, is a hydrogen atom, a $C_{1-8}$ alkyl group or a halogen atom, G is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(9) A method for producing an oligomer of a 9,10-bis (substituted oxy)anthracene compound having repeating units represented by the formula (5), which comprises reacting a 9,10-dihydroxyanthracene compound represented by the following formula (6) and a diglycidyl compound:

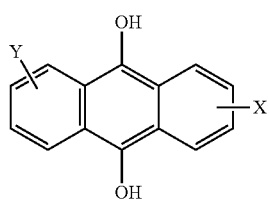

(6)

wherein each of X and Y which may be the same or different, is a hydrogen atom, a $C_{1-8}$ alkyl group or a halogen atom;

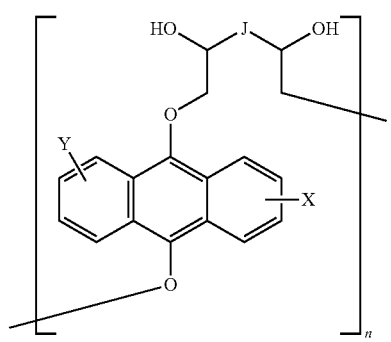

(5)

wherein n represents a repetition number and is from 2 to 50, each of X and Y which may be the same or different, is a hydrogen atom, a $C_{1-8}$ alkyl group or a halogen atom, J is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(10) A photopolymerization sensitizer containing an oligomer of a 9,10-bis(substituted oxy)anthracene compound having repeating units represented by the following formula (1):

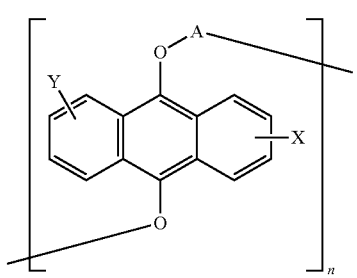

(1)

wherein n represents a repetition number and is from 2 to 50, each of X and Y which may be the same or different, is a hydrogen atom, a $C_{1-8}$ alkyl group or a halogen atom, and A is a bivalent substituent.

(11) A photopolymerization sensitizer containing an oligomer of a 9,10-bis(substituted oxy)anthracene compound having repeating units represented by the following formula (2):

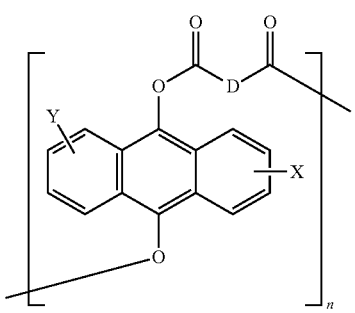

(2)

wherein n represents a repetition number and is from 2 to 50, each of X and Y which may be the same or different, is a hydrogen atom, a $C_{1-8}$ alkyl group or a halogen atom, D is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(12) A photopolymerization sensitizer containing an oligomer of a 9,10-bis(substituted oxy)anthracene compound having repeating units represented by the following formula (3):

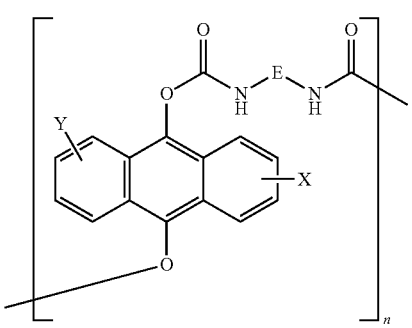

(3)

wherein n represents a repetition number and is from 2 to 50, each of X and Y which may be the same or different, is a hydrogen atom, a $C_{1-8}$ alkyl group or a halogen atom, E is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(13) A photopolymerization sensitizer containing an oligomer of a 9,10-bis(substituted oxy)anthracene compound having repeating units represented by the following formula (4):

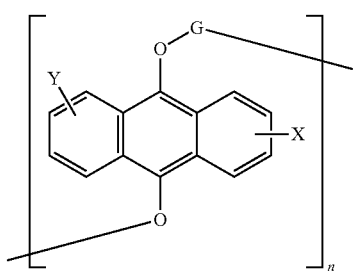

(4)

wherein n represents a repetition number and is from 2 to 50, each of X and Y which may be the same or different, is a hydrogen atom, a $C_{1-8}$ alkyl group or a halogen atom, G is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(14) A photopolymerization sensitizer containing an oligomer of a 9,10-bis(substituted oxy)anthracene compound having repeating units represented by the following formula (5):

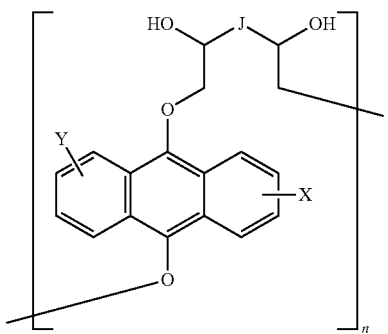

(5)

wherein n represents a repetition number and is from 2 to 50, each of X and Y which may be the same or different, is a hydrogen atom, a $C_{1-8}$ alkyl group or a halogen atom, J is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

(15) A photopolymerization initiator composition, comprising the photopolymerization sensitizer as defined in any one of (10) to (14), and a photopolymerization initiator.

(16) A photopolymerizable composition, comprising the photopolymerization initiator composition as defined in (15), and a photocationic polymerizable compound.

(17) A photopolymerizable composition, comprising the photopolymerization initiator composition as defined in (15), and a photoradical polymerizable compound.

Advantageous Effects of Invention

The oligomer of a 9,10-bis(substituted oxy)anthracene compound of the present invention is a useful compound not only having an effect as a photopolymerization sensitizer in photopolymerization reaction but also having a low degree of migration to a film covering a photopolymerizable composition containing the compound of the present invention as a photopolymerization sensitizer. The objects, characteristics and advantages of the present invention will be clear by the following description in detail.

DESCRIPTION OF EMBODIMENTS (Compound)

The oligomer of a 9,10-bis(substituted oxy)anthracene of the present invention is a compound having repeating units represented by the following formula (1):

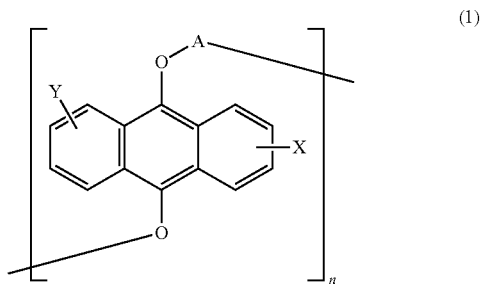

(1)

In the formula (1), n represents a repetition number and is from 2 to 50, each of X and Y which may be the same or different, is a hydrogen atom, a $C_{1-8}$ alkyl group or a halogen atom, and A is a bivalent substituent.

In the formula (1), the $C_{1-8}$ alkyl group represented by X or Y may, for example, be a methyl group, an ethyl group, a n-propyl group, an i-propyl group, a n-butyl group, an i-butyl group, a n-pentyl group, an i-pentyl group, a n-hexyl group, a n-heptyl group, a n-octyl group or a 2-ethylhexyl group, and the halogen atom may be a fluorine atom, a chlorine atom, a bromine atom or an iodine atom. Specific examples of X and Y in the after-described formulae (2) to (6) are the same as these specific examples in the formula (1).

The bivalent substituent represented by A may be a bivalent substituent constituting an ester bond, a urethane bond, an ether bond or the like, formed by a reaction of two hydroxy groups and a bifunctional compound, and for example, the following bivalent substituents may be mentioned.

(A1)

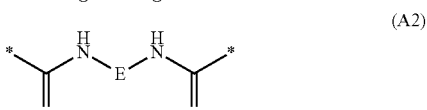

(A2)

(A3)

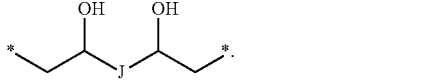

(A4)

In the formulae (A1) to (A4) representing the bivalent substituent, asterisks represent the binding positions of the bivalent substituent, each of D, E, G and J is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

In the formulae (A1) to (A4), the $C_{1-20}$ alkylene group represented by each of D, E, G and J may, for example, be an ethylene group, a propylene group, a butylene group, a pentylene group, a hexylene group, a heptylene group, an octylene group or the following saturated cyclic alkylene group, and the $C_{6-20}$ arylene group may, for example, be a phenylene group or the following arylene group. Such exemplified alkylene group and arylene group may further be substituted by an alkyl group or an alkoxycarbonyl group.

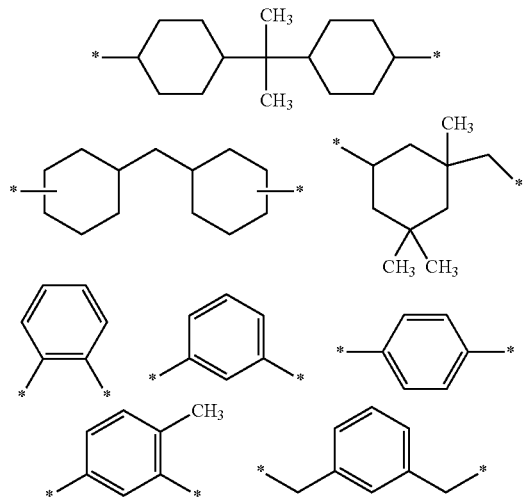

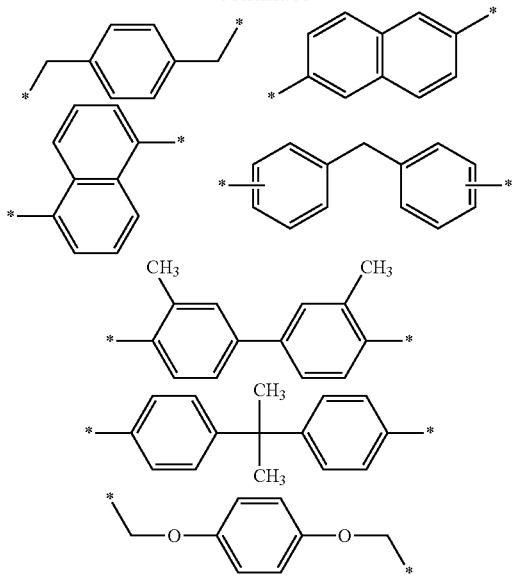

The oligomer of the present invention is an oligomer of a 9,10-bis(substituted oxy)anthracene compound having repeating units of the formula (2) when the bivalent substituent is A1, an oligomer of a 9,10-bis(substituted oxy) anthracene compound having repeating units of the formula (3) when it is A2, an oligomer of a 9,10-bis(substituted oxy)anthracene compound having repeating units of the formula (4) when it is A3, and an oligomer of a 9,10-bis (substituted oxy)anthracene compound having repeating units of the formula (5) when it is A4.

Specific examples of the oligomer of a 9,10-bis(substituted oxy)anthracene compound having repeating units represented by the formula (1) of the present invention are shown. First, specific examples of a compound of the formula (2) wherein A is A1 in the formula (1) are shown in Tables 1 and 2.

TABLE 1

| No. | Basic skeleton | X | Y | D |
|---|---|---|---|---|
| 2-1 | | H | H | — |
| 2-2 | | H | H | *—$CH_2$—* |
| 2-3 | | H | H | *—$CH_2CH_2$—* |
| 2-4 | | H | H | *—$CH_2CH_2CH_2$—* |
| 2-5 | | H | H | *—$CH_2CH(CH_3)$—* |
| 2-6 | | H | H | *—$CH_2CH_2CH_2CH_2$—* |
| 2-7 | | H | H | *—$CH_2CH_2CH_2CH_2CH_2$—* |
| 2-8 | | H | H | *—$CH_2CH_2CH_2CH_2CH_2CH_2$—* |
| 2-9 | | H | H | *—$CH_2CH_2CH_2CH_2CH_2CH_2CH_2$—* |
| 2-10 | | H | H | *—$CH_2CH_2CH_2CH_2CH_2CH_2CH_2CH_2$—* |
| 2-11 | | H | H | (ortho-phenylene) |
| 2-12 | | H | H | (meta-phenylene) |
| 2-13 | | H | H | (para-phenylene) |

TABLE 1-continued

| No. | Basic skeleton | X | Y | D |
|---|---|---|---|---|
| 2-14 | | H | H |  |

"*" represent binding positions, and numeral represents substitution position.

TABLE 2

| No. | Basic skeleton | X | Y | D |
|---|---|---|---|---|
| 2-15 | 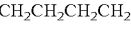 | 2-CH$_3$ | H | *—CH$_2$CH$_2$—* |
| 2-16 | | 2-CH$_3$ | H | *—CH$_2$CH(CH$_3$)—* |
| 2-17 | | 2-CH$_3$ | H | *—CH$_2$CH$_2$CH$_2$CH$_2$—* |
| 2-18 | | 2-CH$_3$ | H | *—CH$_2$CH$_2$CH$_2$CH$_2$CH$_2$CH$_2$—* |
| 2-19 | | 2-CH$_3$ | H | *—CH$_2$CH$_2$CH$_2$CH$_2$CH$_2$CH$_2$CH$_2$CH$_2$—* |
| 2-20 | | 2-CH$_3$ | H |  |
| 2-21 | | 2-CH$_3$ | H |  |
| 2-22 | | 2-CH$_3$CH$_2$ | H | *—CH$_2$CH$_2$—* |
| 2-23 | | 2-CH$_3$CH$_2$ | H | *—CH$_2$CH$_2$CH$_2$CH$_2$—* |
| 2-24 | | 2-CH$_3$CH$_2$ | H | *—CH$_2$CH$_2$CH$_2$CH$_2$CH$_2$CH$_2$—* |
| 2-25 | | 2-CH$_3$CH$_2$ | H | *—CH$_2$CH$_2$CH$_2$CH$_2$CH$_2$CH$_2$CH$_2$CH$_2$—* |
| 2-26 | | 2-CH$_3$CH$_2$ | H | 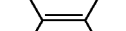 |
| 2-27 | | 2-CH$_3$CH$_2$ | H |  |
| 2-28 | | 2-CH$_3$ | 6-CH$_3$ | *—CH$_2$CH$_2$—* |
| 2-29 | | 2-CH$_3$ | 6-CH$_3$ | *—CH2CH(CH3)—* |
| 2-30 | | 2-CH$_3$ | 6-CH$_3$ | 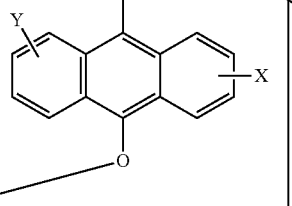 |
| 2-31 | | 2-CH$_3$ | 6-CH$_3$ |  |
| 2-32 | | 2-Cl | H | *—CH$_2$CH$_2$—* |
| 2-33 | | 2-Cl | H | *—CH$_2$CH(CH$_3$)—* |
| 2-34 | | 2-Cl | H | 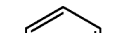 |

TABLE 2-continued

| No. | Basic skeleton | X | Y | D |
|-----|----------------|------|---|---|
| 2-35 | | 2-Cl | H | 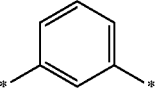 [SMILES: *c1cccc(*)c1] |

"*" represent binding positions, and numeral represents substitution position.

Now, specific examples of a compound of the formula (3) wherein A is A2 in the formula (1) are shown in Tables 3 and 4.

TABLE 3

| No. | Basic skeleton | X | Y | E |
|-----|----------------|---|---|---|
| 3-1 | 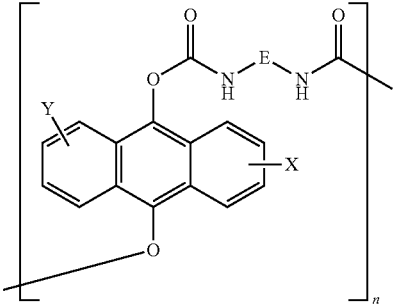 | H | H | *—CH$_2$CH$_2$CH$_2$CH$_2$—* |
| 3-2 | | H | H | *—CH$_2$CH$_2$CH$_2$CH$_2$CH$_2$—* |
| 3-3 | | H | H | *—CH$_2$CH$_2$CH$_2$CH$_2$CH$_2$CH$_2$—* |
| 3-4 | | H | H | *—CH$_2$CH(CH$_3$)CH$_2$C(CH$_3$)$_2$CH$_2$CH$_2$—* |
| 3-5 | | H | H | *—CH(CO$_2$CH$_3$)CH$_2$CH$_2$CH$_2$CH$_2$—* |
| 3-6 | | H | H | 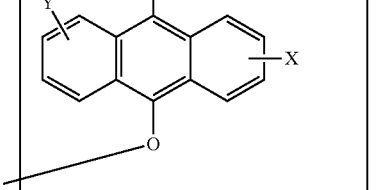 |
| 3-7 | | H | H | 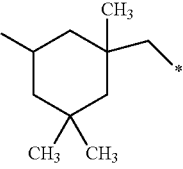 |
| 3-8 | | H | H | 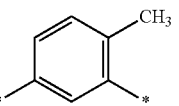 |
| 3-9 | | H | H | 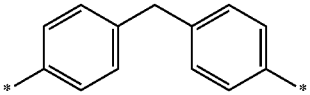 [SMILES: *c1ccc(Cc2ccc(*)cc2)cc1] |
| 3-10 | | H | H | 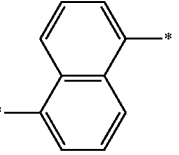 |
| 3-11 | | H | H | 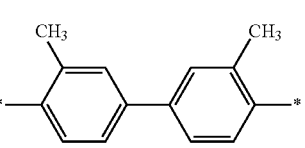 |

"*" represent binding positions, and numeral represents substitution position.

TABLE 4

| No. | Basic skeleton | X | Y | E |
|---|---|---|---|---|
| 3-12 | (see structure below) | 2-CH$_3$ | H | *—CH$_2$CH$_2$CH$_2$CH$_2$CH$_2$CH$_2$—* |
| 3-13 | | 2-CH$_3$ | H | *—CH$_2$CH(CH$_3$)CH$_2$C(CH$_3$)$_2$CH$_2$CH$_2$—* |
| 3-14 | | 2-CH$_3$ | H | (3,3,5-trimethylcyclohexyl-methylene group) |
| 3-15 | | 2-CH$_3$ | H | (2,4-disubstituted toluene) |
| 3-16 | | 2-CH$_3$ | H | (4,4'-methylenediphenyl) |
| 3-17 | | 2-CH$_3$CH$_2$ | H | *—CH$_2$CH$_2$CH$_2$CH$_2$CH$_2$CH$_2$—* |
| 3-18 | | 2-CH$_3$CH$_2$ | H | *—CH$_2$CH(CH$_3$)CH$_2$C(CH$_3$)$_2$CH$_2$CH$_2$—* |
| 3-19 | | 2-CH$_3$CH$_2$ | H | (3,3,5-trimethylcyclohexyl-methylene group) |
| 3-20 | | 2-CH$_3$CH$_2$ | H | (2,4-disubstituted toluene) |
| 3-21 | | 2-CH$_3$CH$_2$ | H | (4,4'-methylenediphenyl) |
| 3-22 | | 2-CH$_3$ | 6-CH$_3$ | *—CH$_2$CH$_2$CH$_2$CH$_2$CH$_2$CH$_2$—* |
| 3-23 | | 2-CH$_3$ | 6-CH$_3$ | *—CH$_2$CH(CH$_3$)CH$_2$C(CH$_3$)$_2$CH$_2$CH$_2$—* |
| 3-24 | | 2-CH$_3$CH$_2$ | 6-CH$_3$ | (3,3,5-trimethylcyclohexyl-methylene group) |
| 3-25 | | 2-CH$_3$CH$_2$ | 6-CH$_3$ | (2,4-disubstituted toluene) |
| 3-26 | | 2-CH$_3$CH$_2$ | 6-CH$_3$ | (4,4'-methylenediphenyl) |
| 3-27 | | 2-Cl | H | *—CH$_2$CH$_2$CH$_2$CH$_2$CH$_2$CH$_2$—* |
| 3-28 | | 2-Cl | H | *—CH$_2$CH(CH$_3$)CH$_2$C(CH$_3$)$_2$CH$_2$CH$_2$—* |

Basic skeleton (for all entries in this table):

[Y—(anthracene-9-yl)—O—C(=O)—NH—E—NH—C(=O)—(anthracene, with X substituent), connected via 10-O to form a polymer of n units]

TABLE 4-continued

| No. | Basic skeleton | X | Y | E |
|---|---|---|---|---|
| 3-29 | | 2-Cl | H | 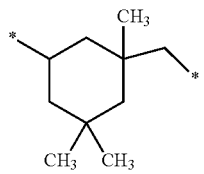 [SMILES: *CC1(C)CC(*)CC(C)(C)C1] |
| 3-30 | | 2-Cl | H | 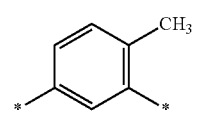 |
| 3-31 | | 2-Cl | H | 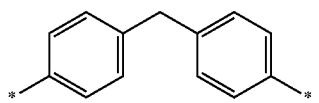 [SMILES: *c1ccc(Cc2ccc(*)cc2)cc1] |

"*" represent binding positions, and numeral represents substitution position.

"*" represent binding positions, and numeral represents substitution position.

Now, specific examples of a compound of the formula (4) wherein A is A3 in the formula (1) are shown in Tables 5 and 6.

TABLE 5

| No. | Basic skeleton | X | Y | G |
|---|---|---|---|---|
| 4-1 | 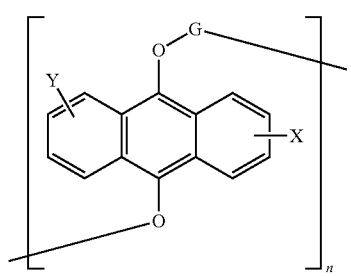 | H | H | *—CH$_2$CH$_2$—* |
| 4-2 | | H | H | *—CH$_2$CH$_2$CH$_2$—* |
| 4-3 | | H | H | *—CH$_2$CH(CH$_3$)—* |
| 4-4 | | H | H | *—CH$_2$CH$_2$CH$_2$CH$_2$—* |
| 4-5 | | H | H | *—CH$_2$C(CH$_3$)$_2$CH$_2$—* |
| 4-6 | | H | H | *—CH$_2$CH$_2$CH$_2$CH$_2$CH$_2$—* |
| 4-7 | | H | H | *—CH$_2$CH$_2$CH$_2$CH$_2$CH$_2$CH$_2$—* |
| 4-8 | | H | H | *—CH$_2$CH$_2$CH(CH$_3$)CH$_2$CH$_2$—* |
| 4-9 | | H | H | *—CH$_2$CH$_2$CH$_2$CH$_2$CH$_2$CH$_2$CH$_2$—* |
| 4-10 | | H | H | *—CH$_2$CH$_2$CH$_2$CH$_2$CH$_2$CH$_2$CH$_2$CH$_2$—* |
| 4-11 | | H | H | *—CH$_2$CH$_2$CH$_2$CH$_2$CH$_2$CH$_2$CH$_2$CH$_2$CH$_2$—* |
| 4-12 | | H | H | *—CH$_2$CH$_2$CH$_2$CH$_2$CH$_2$CH$_2$CH$_2$CH$_2$CH$_2$CH$_2$—* |
| 4-13 | | H | H | 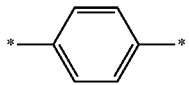 |
| 4-14 | | H | H | 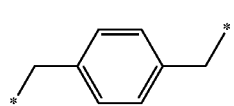 [SMILES: *Cc1ccc(C*)cc1] |

"*" represent binding positions, and numeral represents substitution position.

TABLE 6

| No. | Basic skeleton | X | Y | G |
|---|---|---|---|---|
| 4-15 | 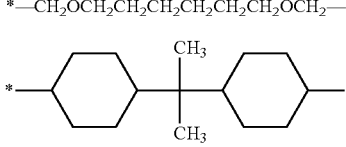 | 2-CH$_3$ | H | *—CH$_2$CH$_2$—* |
| 4-16 | | 2-CH$_3$ | H | *—CH$_2$CH$_2$CH$_2$—* |
| 4-17 | | 2-CH$_3$ | H | *—CH$_2$CH$_2$CH$_2$CH$_2$CH$_2$—* |
| 4-18 | | 2-CH$_3$ | H | *—CH$_2$C(CH$_3$)$_2$CH$_2$—* |
| 4-19 | | 2-CH$_3$ | H | *—CH$_2$CH$_2$CH(CH$_3$)CH$_2$CH$_2$—* |
| 4-20 | | 2-CH$_3$ | H | *—CH$_2$CH$_2$CH$_2$CH$_2$CH$_2$CH$_2$CH$_2$—* |
| 4-21 | | 2-CH$_3$ | H | *—CH$_2$CH$_2$CH$_2$CH$_2$CH$_2$CH$_2$CH$_2$CH$_2$—* |
| 4-22 | | 2-CH$_3$ | H | *—CH$_2$CH$_2$CH$_2$CH$_2$CH$_2$CH$_2$CH$_2$CH$_2$CH$_2$CH$_2$—* |
| 4-23 | | 2-CH$_3$CH$_2$ | H | *—CH$_2$CH$_2$—* |
| 4-24 | | 2-CH$_3$CH$_2$ | H | *—CH$_2$CH$_2$CH$_2$—* |
| 4-25 | | 2-CH$_3$CH$_2$ | H | *—CH$_2$CH$_2$CH$_2$CH$_2$CH$_2$—* |
| 4-26 | | 2-CH$_3$CH$_2$ | H | *—CH$_2$C(CH$_3$)$_2$CH$_2$—* |
| 4-27 | | 2-CH$_3$CH$_2$ | H | *—CH$_2$CH$_2$CH(CH$_3$)CH$_2$CH$_2$—* |
| 4-28 | | 2-CH$_3$CH$_2$ | H | *—CH$_2$CH$_2$CH$_2$CH$_2$CH$_2$CH$_2$CH$_2$—* |
| 4-29 | | 2-CH$_3$CH$_2$ | H | *—CH$_2$CH$_2$CH$_2$CH$_2$CH$_2$CH$_2$CH$_2$CH$_2$—* |
| 4-30 | | 2-CH$_3$CH$_2$ | H | *—CH$_2$CH$_2$CH$_2$CH$_2$CH$_2$CH$_2$CH$_2$CH$_2$CH$_2$CH$_2$—* |
| 4-31 | | 2-CH$_3$ | 6-CH$_3$ | *—CH$_2$CH$_2$—* |
| 4-32 | | 2-CH$_3$ | 6-CH$_3$ | *—CH$_2$CH$_2$CH$_2$—* |
| 4-33 | | 2-CH$_3$ | 6-CH$_3$ | *—CH$_2$CH$_2$CH$_2$CH$_2$CH$_2$—* |
| 4-34 | | 2-CH$_3$ | 6-CH$_3$ | *—CH$_2$C(CH$_3$)$_2$CH$_2$—* |
| 4-35 | | 2-CH$_3$ | 6-CH$_3$ | *—CH$_2$CH$_2$CH(CH$_3$)CH$_2$CH$_2$—* |
| 4-36 | | 2-CH$_3$ | 6-CH$_3$ | *—CH$_2$CH$_2$CH$_2$CH$_2$CH$_2$CH$_2$CH$_2$—* |
| 4-37 | | 2-CH$_3$ | 6-CH$_3$ | *—CH$_2$CH$_2$CH$_2$CH$_2$CH$_2$CH$_2$CH$_2$CH$_2$—* |
| 4-38 | | 2-CH$_3$ | 6-CH$_3$ | *—CH$_2$CH$_2$CH$_2$CH$_2$CH$_2$CH$_2$CH$_2$CH$_2$CH$_2$CH$_2$—* |
| 4-39 | | 2-Cl | H | *—CH$_2$CH$_2$—* |
| 4-40 | | 2-Cl | H | *—CH$_2$CH$_2$CH$_2$—* |
| 4-41 | | 2-Cl | H | *—CH$_2$CH$_2$CH$_2$CH$_2$—* |
| 4-42 | | 2-Cl | H | *—CH$_2$C(CH$_3$)$_2$CH$_2$—* |
| 4-43 | | 2-Cl | H | *—CH$_2$CH$_2$CH(CH$_3$)CH$_2$CH$_2$—* |
| 4-44 | | 2-Cl | H | *—CH$_2$CH$_2$CH$_2$CH$_2$CH$_2$CH$_2$CH$_2$—* |
| 4-45 | | 2-Cl | H | *—CH$_2$CH$_2$CH$_2$CH$_2$CH$_2$CH$_2$CH$_2$CH$_2$—* |
| 4-46 | | 2-Cl | H | *—CH$_2$CH$_2$CH$_2$CH$_2$CH$_2$CH$_2$CH$_2$CH$_2$CH$_2$CH$_2$—* |

"*" represent binding positions, and numeral represents substitution position.

Further, specific examples of a compound of the formula (5) wherein A is A4 in the formula (1) are shown in Tables 7 and 8.

TABLE 7

| No. | Basic skeleton | X | Y | J |
|---|---|---|---|---|
| 5-1 | 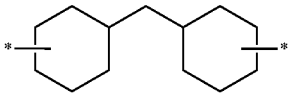 | H | H | *—CH$_2$OCH$_2$CH$_2$OCH$_2$—* |
| 5-2 | | H | H | *—CH$_2$OCH$_2$C(CH$_3$)$_2$CH$_2$OCH$_2$—* |
| 5-3 | | H | H | *—CH$_2$OCH$_2$CH$_2$OCH$_2$CH$_2$OCH$_2$—* |
| 5-4 | | H | H | *—CH$_2$OCH$_2$CH$_2$CH$_2$CH$_2$OCH$_2$—* |
| 5-5 | | H | H | *—CH$_2$OCH$_2$CH$_2$CH$_2$CH$_2$CH$_2$CH$_2$OCH$_2$—* |
| 5-6 | | H | H | 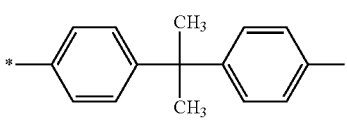 |
| 5-7 | | H | H | 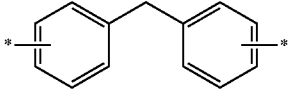 |
| 5-8 | | H | H | *—C$_6$H$_4$—C(CH$_3$)$_2$—C$_6$H$_4$—* |
| 5-9 | | H | H | *—C$_6$H$_4$—CH$_2$—C$_6$H$_4$—* |

TABLE 7-continued

| No. | Basic skeleton | X | Y | J |
|---|---|---|---|---|
| 5-10 | | H | H |  |

"*" represent binding positions, and numeral represents substitution position.

TABLE 8

| No. | Basic skeleton | X | Y | J |
|---|---|---|---|---|
| 5-11 | (anthracene-based polymer skeleton with HO-J-OH bridge, Y and X substituents, and O linkage, repeating n times) | 2-$CH_3$ | H | *—$CH_2OCH_2CH_2OCH_2$—* |
| 5-12 | | 2-$CH_3$ | H | *—$CH_2OCH_2C(CH_3)_2CH_2OCH_2$—* |
| 5-13 | | 2-$CH_3$ | H | *—cyclohexyl—C($CH_3$)$_2$—cyclohexyl—* |
| 5-14 | | 2-$CH_3CH_2$ | H | *—$CH_2OCH_2CH_2OCH_2$—* |
| 5-15 | | 2-$CH_3CH_2$ | H | *—$CH_2OCH_2C(CH_3)_2CH_2OCH_2$—* |
| 5-16 | | 2-$CH_3CH_2$ | H | *—cyclohexyl—C($CH_3$)$_2$—cyclohexyl—* |
| 5-17 | | 2-$CH_3$ | 6-$CH_3$ | *—$CH_2OCH_2CH_2OCH_2$—* |
| 5-18 | | 2-$CH_3$ | 6-$CH_3$ | *—$CH_2OCH_2C(CH_3)_2CH_2OCH_2$—* |
| 5-19 | | 2-$CH_3$ | 6-$CH_3$ | *—cyclohexyl—C($CH_3$)$_2$—cyclohexyl—* |
| 5-20 | | 2-Cl | H | *—$CH_2OCH_2CH_2OCH_2$—* |
| 5-21 | | 2-Cl | H | *—$CH_2OCH_2C(CH_3)_2CH_2OCH_2$—* |
| 5-22 | | 2-Cl | H | *—cyclohexyl—C($CH_3$)$_2$—cyclohexyl—* |

"*" represent binding positions, and numeral represents substitution position.

Among such exemplified compounds, the following 46 compounds are preferred in that they are easily produced and have a high effect as a photopolymerization sensitizer.
(2-3)
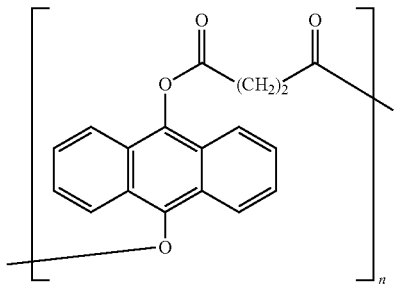
(2-5)
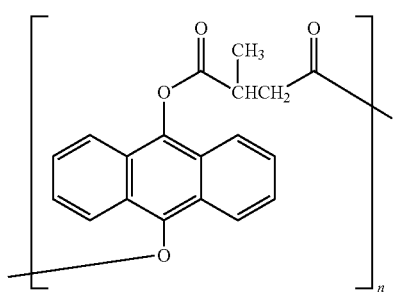
(2-6)
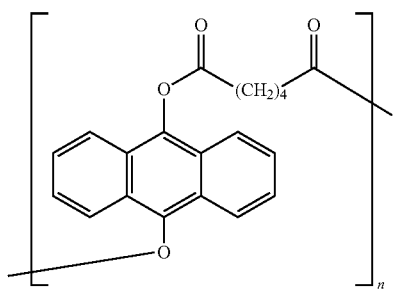
(2-8)
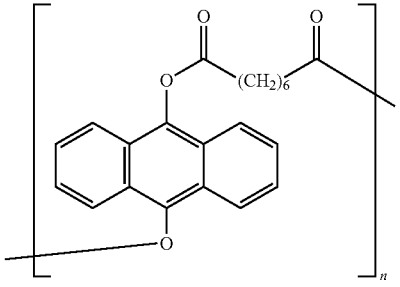
(2-10)
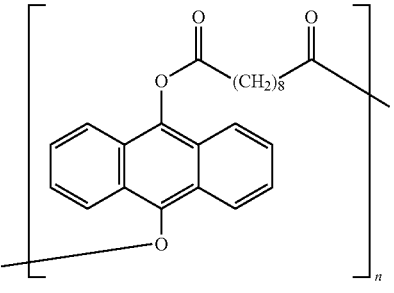
-continued
(2-11)
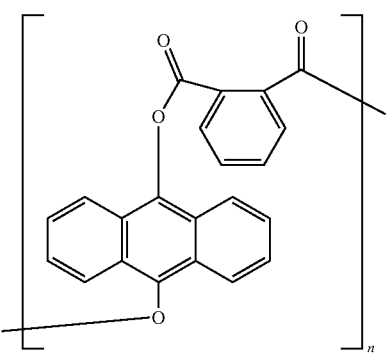
(2-15)
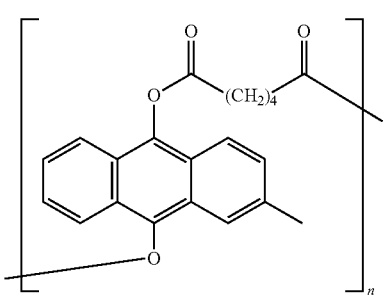
(2-17)
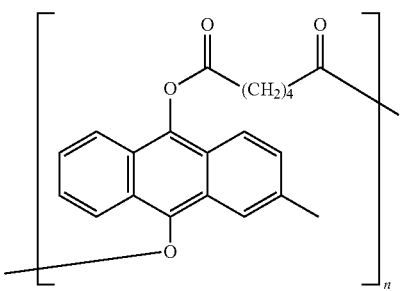
(2-18)
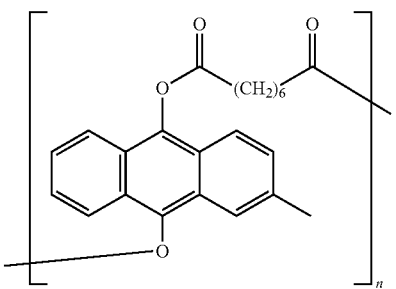
(2-19)
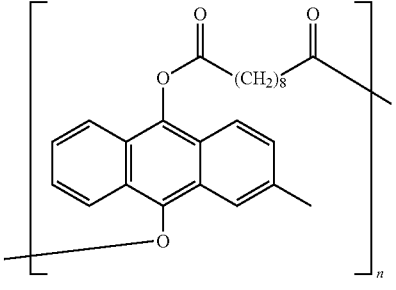

(2-22)
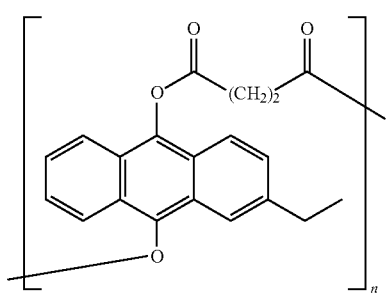
(2-23)
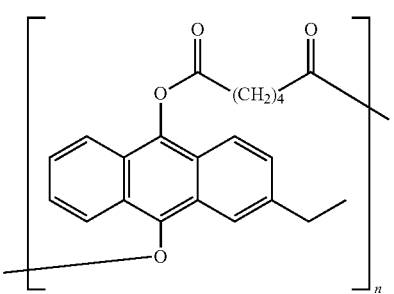
(2-24)
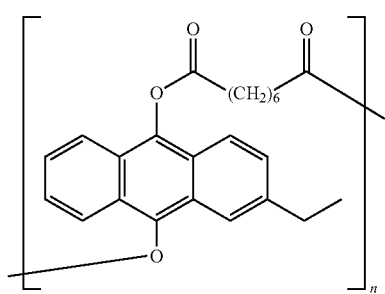
(2-25)
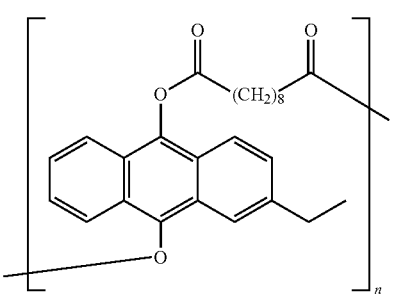
(3-3)
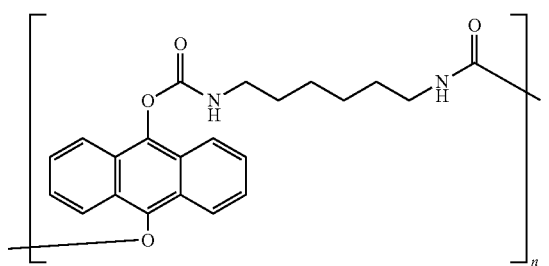
(3-4)
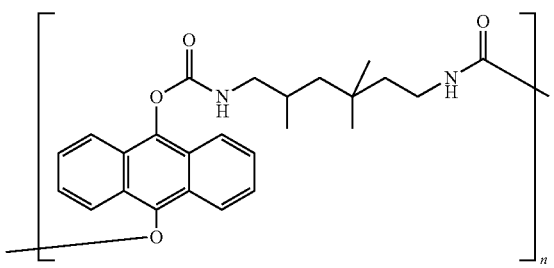
(3-6)
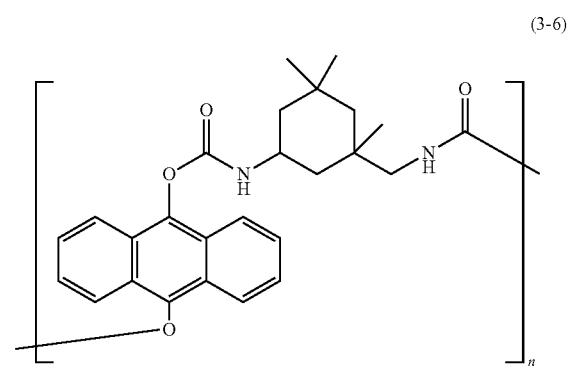
(3-7)
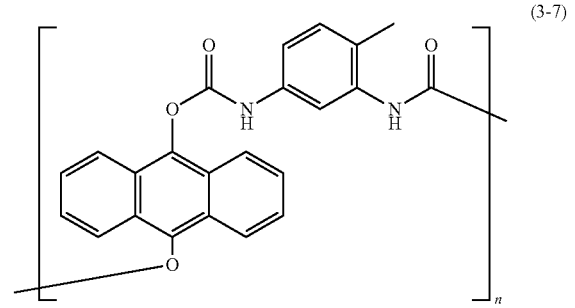
(3-8)
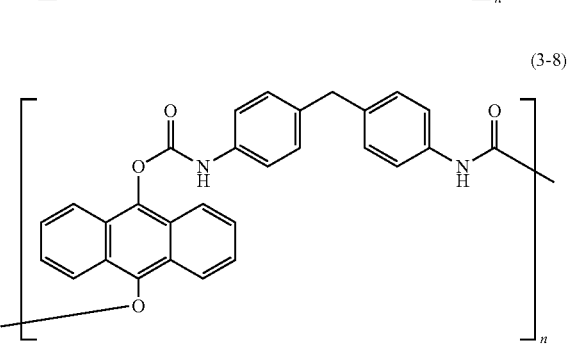
(3-13)
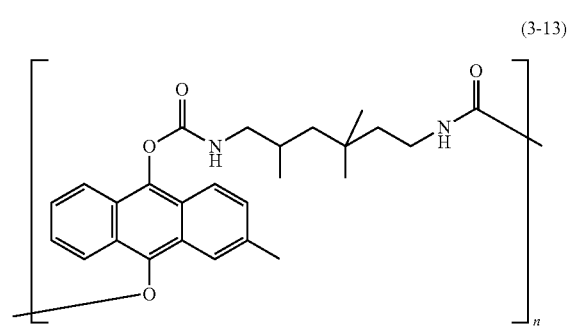

(3-14)
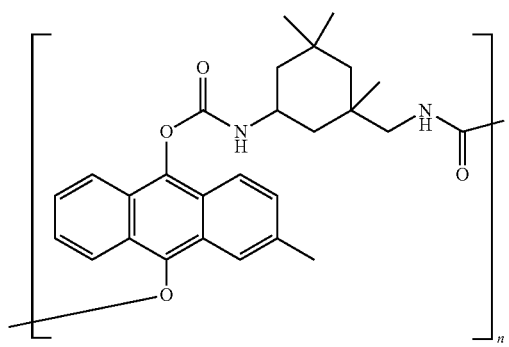
(3-15)
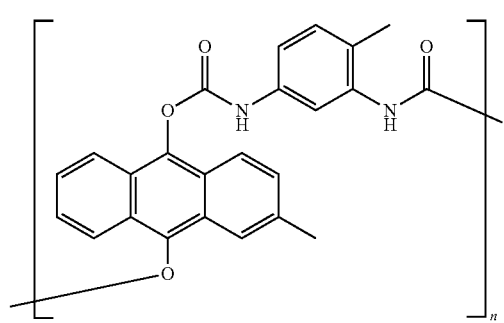
(3-18)
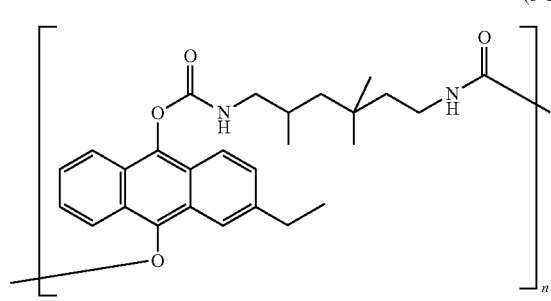
(3-19)
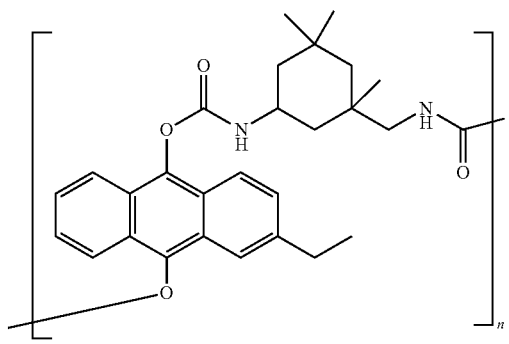
(3-20)
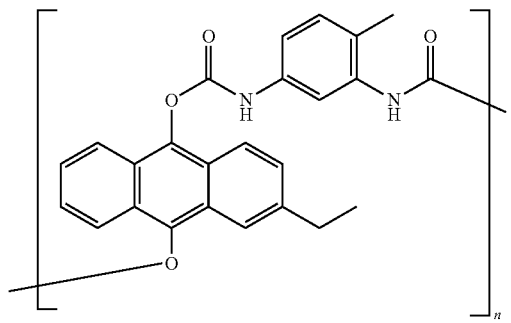
(4-4)
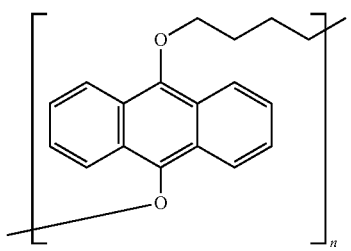
(4-6)
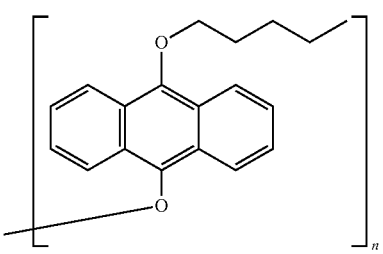
(4-8)
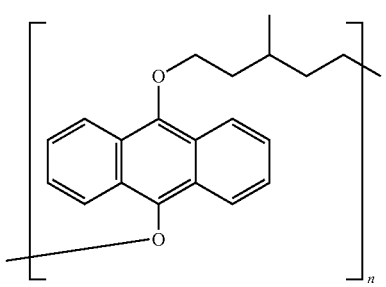
(4-10)
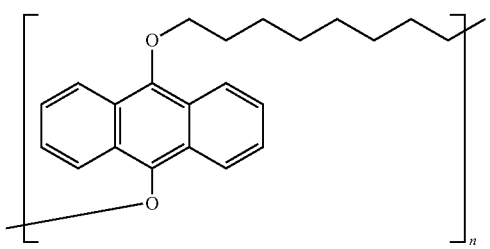

(4-11)
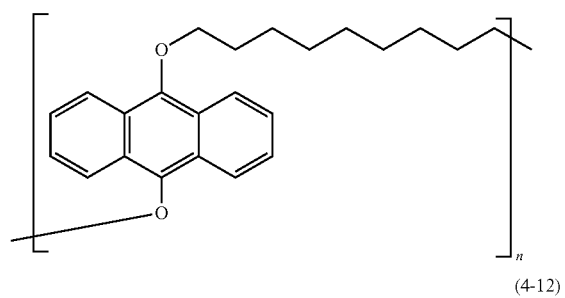
(4-21)
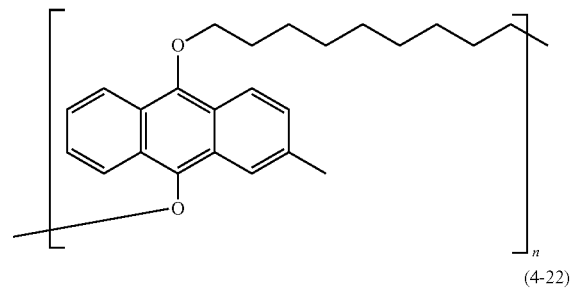
(4-12)
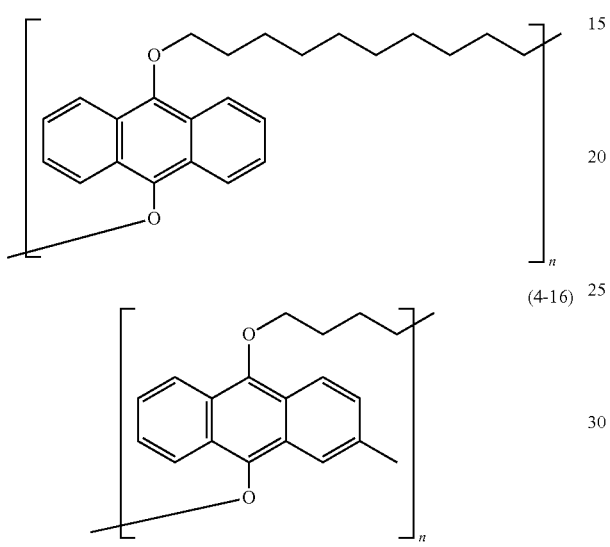
(4-22)
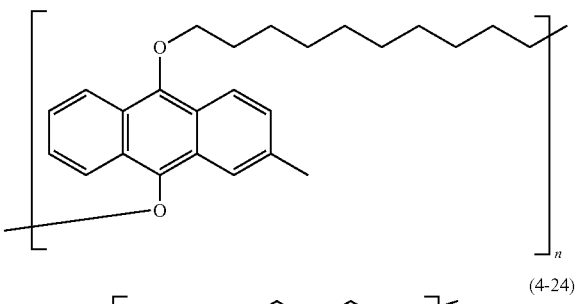
(4-16)
(4-17)
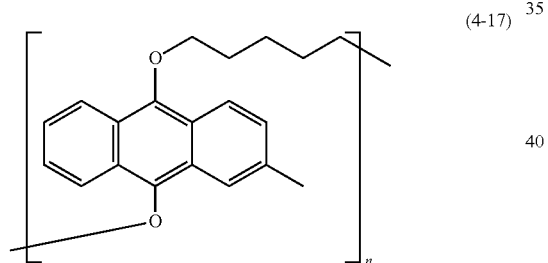
(4-24)
(4-25)
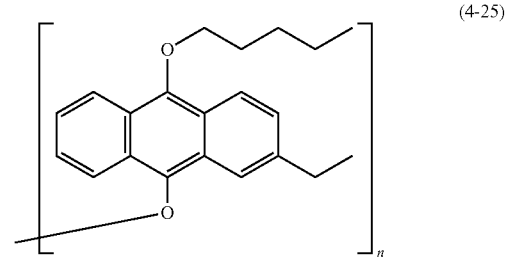
(4-19)
(4-20)
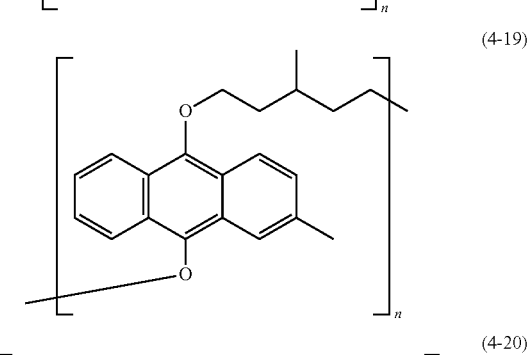
(4-27)
(4-28)
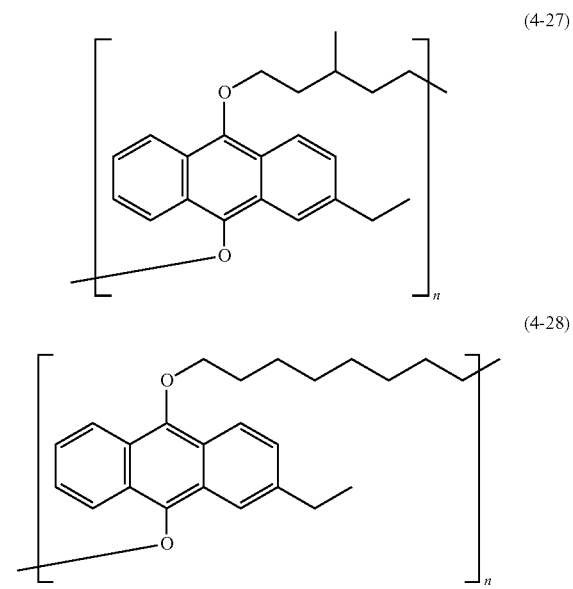

-continued

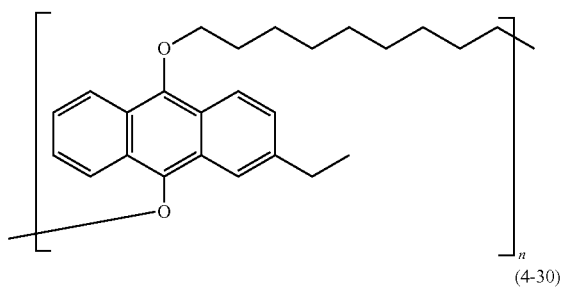
(4-29)

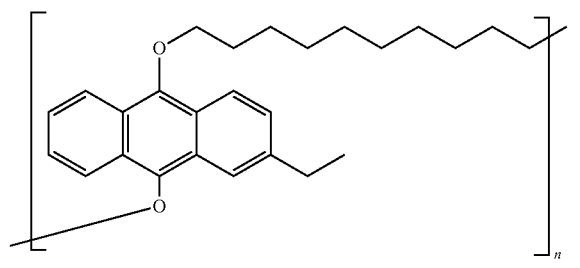
(4-30)

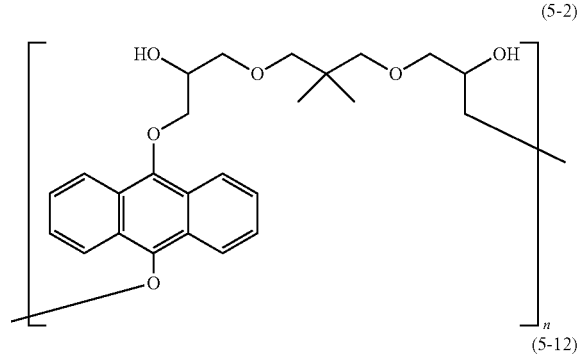
(5-2)

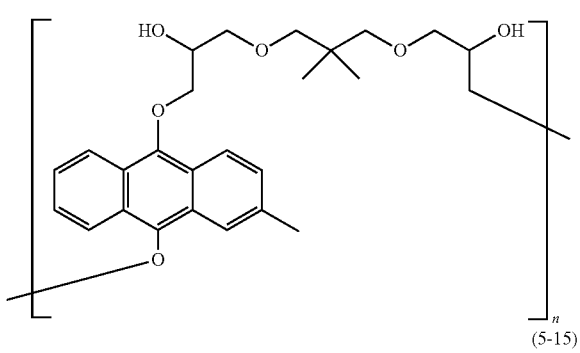
(5-12)

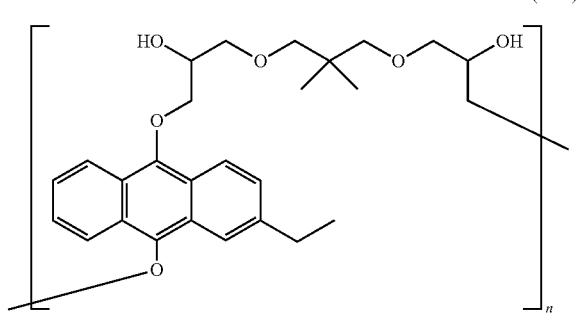
(5-15)

Among the above mentioned preferred compounds, particularly preferred are the oligomer of Compound No. 2-6, the oligomer of Compound No. 2-10, the oligomer of Compound No. 2-17, the oligomer of Compound No. 2-23, the oligomer of Compound No. 2-25, the oligomer of Compound No. 3-4, the oligomer of Compound No. 3-6, the oligomer of Compound No. 3-7, the oligomer of Compound No. 4-4, the oligomer of Compound No. 4-6, the oligomer of Compound No. 4-8, the oligomer of Compound No. 4-10, the oligomer of Compound No. 4-11, the oligomer of Compound No. 4-12 and the oligomer of Compound No. 5-2.

(Production Method)

Now, the method for producing the oligomer of a 9,10-bis(substituted oxy)anthracene compound of the present invention will be described. The oligomer of a 9,10-bis(substituted oxy)anthracene compound of the present invention can be obtained by reacting a 9,10-dihydroxyanthracene compound represented by the formula (6) and a corresponding bifunctional compound in the presence of a catalyst or without catalyst in accordance with the following reaction scheme 1.

The bifunctional compound may be any compound having at least two functional groups reactive with a hydroxy group to form a bond. It may, for example, be a dibasic acid having at least two carboxy groups reactive with a hydroxy group, a dibasic acid halide or a dibasic acid ester, a diisocyanate compound having at least two isocyanate groups reactive with a hydroxy group to form a urethane bond, a dihalogen compound or a diol compound reactive with a hydroxy group, or a diglycidyl compound.

Reaction scheme 1

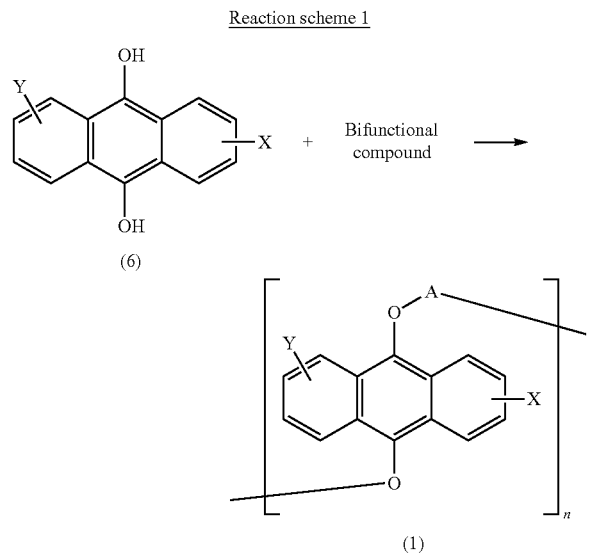

In the reaction scheme 1, n represents a repetition number and is from 2 to 50, each of X and Y which may be the same or different, is a hydrogen atom, a $C_{1-8}$ alkyl group or a halogen atom, and A is a bivalent substituent.

(Method for Producing Compound of the Formula (6))

In the reaction scheme 1, the 9,10-dihydroxyanthracene compound represented by the formula (6) used as a raw material is obtained by reducing a 9,10-anthraquinone compound. The reducing agent may, for example, be hydrosulfite, hydrogen reduction using palladium/carbon as a catalyst, or thiourea dioxide.

The 9,10-anthraquinone compound as a raw material in the reaction scheme may, for example, be specifically 9,10-anthraquinone, 2-methyl-9,10-anthraquinone, 2-ethyl-9,10- anthraquinone, 2-t-pentyl-9,10-anthraquinone, 2,6-dimethyl-9,10-anthraquinone, 2-chloro-9,10-anthraquinone, or 2-bromo-9,10-anthraquinone.

Further, in the case of 9,10-dihydroxyanthracene, as an industrial method, 9,10-anthraquinone is reduced by using an alkali metal salt of 1,4,4a,9a-tetrahydroanthraquinone which is a Diels-Alder reaction product of 1,4-naphthoquinone and 1,3-butadiene or its isomer 1,4-dihydro-9,10-dihydroxyanthracene, whereby 9,10-dihydroxyanthracene can be obtained more easily. That is, an aqueous solution of an alkali metal salt of 9,10-dihydroxyanthracene can be obtained by reacting 1,4,4a,9a-tetrahydroanthraquinone obtained by reaction of 1,4-naphthoquinone and 1,3-butadiene with 9,10-anthraquinone in an aqueous medium in the presence of an alkaline compound such as an alkali metal hydroxide.

The aqueous solution of an alkali metal salt of 9,10-dihydroxyanthracene obtained by this reaction is acidified in the absence of oxygen, whereby precipitates of 9,10-dihydroxyanthracene can be obtained. By purifying the precipitates, 9,10-dihydroxyanthracene can be obtained. A 9,10-dihydroxyanthracene compound having a substituent may be obtained in the same manner.

A 9,10-dihydroxyanthracene compound of the formula (6) can be obtained in such a manner.

A typical 9,10-dihydroxyanthracene compound may, for example, be 9,10-dihydroxyanthracene, 2-methyl-9,10-dihydroxyanthracene, 2-ethyl-9,10-dihydroxyanthracene, 2-t-pentyl-9,10-dihydroxyanthracene, 2,6-dimethyl-9,10-dihydroxyanthracene, 2-chloro-9,10-dihydroxyanthracene or 2-bromo-9,10-dihydroxyanthracene.

(Method for Producing Compound of the Formula (1))

Then, the 9,10-dihydroxyanthracene compound represented by the formula (6) is reacted with a bifunctional compound in accordance with the reaction scheme 1 in the presence of a catalyst or without catalyst to obtain an oligomer of a 9,10-bis(substituted oxy)anthracene compound having repeating units represented by the formula (1):

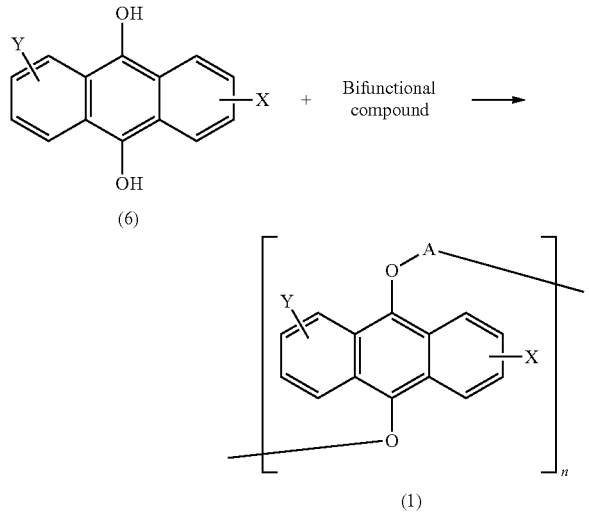

In the reaction scheme 1, n represents a repetition number and is from 2 to 50, each of X and Y which may be the same or different, is a hydrogen atom, a $C_{1-8}$ alkyl group or a halogen atom, and A is a bivalent substituent.

The bifunctional compound used in the reaction scheme 1 may be a dibasic acid, a dibasic acid halide or dibasic acid ester, a diisocyanate compound, a dihalogen compound or a diol compound, or a diglycidyl compound.

As shown in the following reaction scheme 2, when a dibasic acid, a dibasic acid halide or a dibasic acid ester is used as the bifunctional compound, an oligomer of a 9,10-bis(substituted oxy)anthracene compound having repeating units of the formula (2) is obtained.

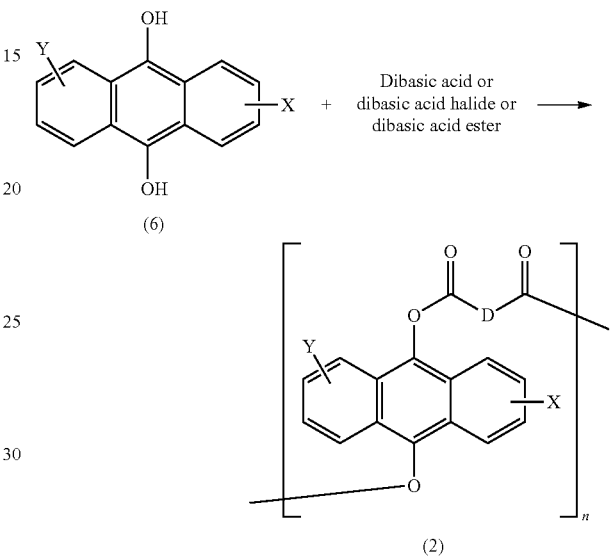

In the reaction scheme 2, n represents a repetition number and is from 2 to 50, each of X and Y which may be the same or different, is a hydrogen atom, a $C_{1-8}$ alkyl group or a halogen atom, D is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

The dibasic acid may, for example, be oxalic acid, malonic acid, succinic acid, glutaric acid, adipic acid, pimelic acid, suberic acid, azelaic acid, sebacic acid, dodecanedioic acid, phthalic acid, isophthalic acid, terephthalic acid or naphthalene dicarboxylic acid. The dibasic acid halide may, for example, be succinic acid chloride, adipic acid chloride, sebacoyl chloride, phthalic acid chloride, isophthalic acid chloride or terephthalic acid chloride. The dibasic acid ester may, for example, be dimethyl oxalate, diethyl oxalate, dimethyl malonate, diethyl malonate, dimethyl succinate, diethyl succinate, dimethyl adipate, diethyl adipate, di-2-ethylhexyl adipate, dimethyl 2-methyl succinate, dimethyl phthalate, diethyl phthalate, di-2-ethylhexyl phthalate, dimethyl isophthalate, diethyl isophthalate or di-2-ethylhexyl isophthalate.

In the reaction with the dibasic acid, the dibasic acid halide or the dibasic acid ester, the reaction rate increases, and efficient production is possible by using a base or a catalyst. The catalyst used for the reaction with the dibasic acid may, for example, be a mineral acid (sulfuric acid, hydrochloric acid), an organic acid (methanesulfonic acid, p-toluenesulfonic acid), a Lewis acid (boron fluoride etherate, aluminum trichloride, titanium tetrachloride, iron trichloride or zinc dichloride), a solid acid catalyst (manufactured by Futamura Chemical Co., Ltd.), Amberlist (manufactured by ORGANO CORPORATION), Nafion (manufactured by DuPont, registered trademark), a titanium tetraalkoxide compound (titanium tetraisopropoxide, titanium tetra-n-butoxide or titanium tetramethoxide) or an organic tin compound (dibutyltin dilaurate, dibutyltin oxide). The base to be used in the reaction with the dibasic acid halide may, for example, be an inorganic base (sodium hydroxide, potassium hydroxide, sodium carbonate, potassium carbonate or sodium bicarbonate), an organic base (pyridine, dimethylaminopyridine, triethylamine, ethyldiisopropylamine or triphenylphosphine). The catalyst to be used in the reaction with the dibasic acid ester may, for example, be a mineral acid (sulfuric acid, hydrochloric acid), an organic acid (methanesulfonic acid, p-toluenesulfonic acid), a Lewis acid (boron fluoride etherate, aluminum trichloride, titanium tetrachloride, iron trichloride or zinc dichloride), a solid acid catalyst (manufactured by Futamura Chemical Co., Ltd.), Amberlist (manufactured by ORGANO CORPORATION), Nafion (manufactured by DuPont), a titanium tetraalkoxide compound (titanium tetraisopropoxide, titanium tetra-n-butoxide or titanium tetramethoxide), an organic tin compound (dibutyltin dilaurate or dibutyltin oxide) or a basic compound (sodium hydroxide, potassium hydroxide, sodium methoxide or sodium ethoxide).

The amount of the catalyst added is preferably at least 0.01 mol % and less than 20 mol %, more preferably at least 0.1 mol % and less than 10 mol %, to the 9,10-dihydroxyanthracene compound. If it is less than 0.01 mol %, the reaction rate is low, and if it is at least 20 mol %, the purity of the product may decrease.

The amount of the base added is preferably at least 2.0 molar times and less than 20.0 molar times, more preferably at least 3.0 molar times and less than 10.0 molar times, to the 9,10-dihydroxyanthracene compound. If it is less than 2.0 molar times, the reaction will not be completed, and if it is at least 20.0 molar times, side reaction may occur, and the yield and the purity will decrease.

In a case where the 9,10-dihydroxyanthracene compound is dissolved in an aqueous solution of an inorganic base and is reacted with the dibasic acid, the dibasic acid halide or the dibasic acid ester, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate will be low, and if it is at least 1.0 molar times, the purity of the product will decrease.

The amount of the dibasic acid, the dibasic acid halide or the dibasic acid ester added to the 9,10-dihydroxyanthracene compound represented by the formula (6) is at least 0.5 molar times and at most 5.0 molar times, preferably at least 1.0 molar times and at most 3.0 molar times. If it is less than 0.5 molar times, the average molecular weight tends to be low, and the migration property cannot be suppressed, and further, an unreacted 9,10-dihydroxyanthracene compound will remain in the product, thus lowering the purity. Further, if it exceeds 5.0 molar times, the average molecular weight tends to be low, and the migration property cannot be suppressed, and in addition, an unreacted dibasic acid, dibasic acid halide or dibasic acid ester will remain in the product, thus lowering the purity.

Further, as the molar ratio of the dibasic acid, the dibasic acid halide or the dibasic acid ester to the 9,10-dihydroxyanthracene compound represented by the formula (6) is closer to 1, the average molecular weight tends to be too high, the mobility of the molecules will be lower, and the sensitizing performance may decrease. In such a case, a monobasic acid, a monobasic acid halide or a monobasic acid ester may be added in a small amount to adjust the molecular weight.

The reaction is carried out in a solvent or without solvent. The solvent used is not particularly limited so long as it does not react with the dibasic acid, a dibasic acid halide or the dibasic acid ester used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, a halogenated hydrocarbon solvent such as methylene chloride, ethylene dichloride or chlorobenzene, or water.

The reaction temperature of this reaction is, in the case of the reaction with the dibasic acid or the dibasic acid ester, usually at least 50° C. and at most 250° C., preferably at least 100° C. and at most 200° C. If it is less than 50° C., the reaction will take too long, and if it exceeds 200° C., impurities tend to increase and the purity of the desired compound will decrease.

In the case of the reaction with the dibasic acid halide, the reaction temperature is usually at least 0° C. and at most 100° C., preferably at least 10° C. and less than 30° C. If it is less than 0° C., the reaction will take too long, and if it exceeds 100° C., impurities tend to increase, and the purity of the desired compound will decrease.

The reaction time in the reaction varies depending upon the reaction temperature and is usually from about 0.5 hour to about 30 hours. It is preferably from 1 hour to 10 hours.

After completion of the reaction, as the case requires, unreacted raw material, the solvent and the catalyst are removed by washing, by vacuum distillation, by filtration or the like alone or in combination. In a case where the product is a solid, crystals precipitated after the reaction may be subjected to filtration and dried, or dried up as they are, whereby crystals can be obtained. In a case where the formed product is a liquid, it is dried up as it is, followed by purification such as distillation as the case requires, to obtain an oligomer of a 9,10-bis(substituted oxy)anthracene compound.

Further, in a case where a diisocyanate compound is used as the bifunctional compound, as shown in the following reaction scheme 3, an oligomer of a 9,10-bis(substituted oxy)anthracene compound having repeating units of the formula (3) is obtained.

Reaction scheme 3

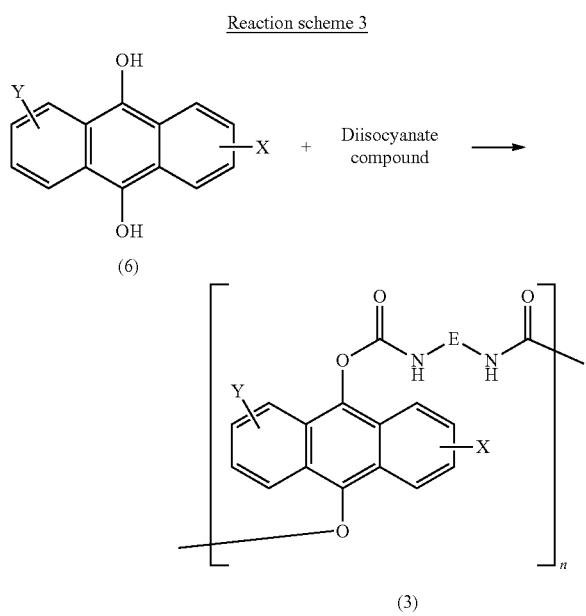

(6)

(3)

In the reaction scheme 3, n represents a repetition number and is from 2 to 50, each of X and Y which may be the same or different, is a hydrogen atom, a $C_{1-8}$ alkyl group or a halogen atom, E is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

The diisocyanate compound may be any of an aliphatic diisocyanate, an alicyclic diisocyanate and an aromatic diisocyanate. The aliphatic diisocyanate may, for example, be tetramethylene-1,4-diisocyanate, pentamethylene-1,5-diisocyanate, hexamethylene diisocyanate, 2,4,4-trimethylhexamethylene diisocyanate (TMHMDI) or lysine diisocyanate. The alicyclic diisocyanate may, for example, be isophorone diisocyanate, hydrogenated xylylene diisocyanate, hydrogenated diphenylmethane diisocyanate or 1,4-diisocyanate cyclohexane. The aromatic diisocyanate may, for example, be 2,4-toluene diisocyanate, 2,6-toluene diisocyanate, diphenylmethane diisocyanate, 1,5-naphthalene diisocyanate, tolidine diisocyanate, xylylene diisocyanate or tetramethylxylylene diisocyanate (reaction scheme 3).

In the reaction with the diisocyanate compound, the reaction rate will increase and effective production will be possible by using a catalyst. The catalyst used for the reaction with the diisocyanate compound is an organic tin compound or a basic compound. The organic tin compound may, for example, be dibutyltin dilaurate (DBTBL) or dibutyltin oxide, and the basic compound may, for example, be triethylamine, tributylamine, trihexylamine, dimethylamine, diethylamine, dipropylamine, dibutylamine, cyclohexylamine, pyridine, piperidine, γ-picoline or lutidine.

The amount of the catalyst added is preferably at least 0.01 mol % and less than 20 mol %, more preferably at least 0.1 mol % and less than 10 mol % to the 9,10-dihydroxyanthracene compound. If it is less than 0.01 mol %, the reaction rate will be low, and if it is at least 20 mol %, the purity of the formed product will decrease.

In a case where the 9,10-dihydroxyanthracene compound is dissolved in an aqueous solution of an inorganic base and is reacted with the diisocyanate compound, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate will be low, and if it is at least 1.0 molar times, the purity of the product will decrease.

The amount of the diisocyanate compound added to the 9,10-dihydroxyanthracene compound represented by the formula (6) is at least 0.5 molar times and at most 5.0 molar times, preferably at least 1.0 molar times and at most 3.0 molar times. If it is less than 0.5 molar times, the average molecular weight tends to be low, and the migration property cannot be suppressed, and further, an unreacted 9,10-dihydroxyanthracene compound will remain in the product, thus lowering the purity. Further, if it exceeds 5.0 molar times, the average molecular weight tends to be low, and the migration property cannot be suppressed, and in addition, an unreacted diisocyanate compound will remain in the product, thus lowering the purity.

Further, as the molar ratio of the diisocyanate compound to the 9,10-dihydroxyanthracene compound represented by the formula (6) is closer to 1, the average molecular weight tends to be too high, the mobility of the molecules will be lower, and the sensitizing performance may decrease. In such a case, a monoisocyanate compound may be added in a small amount to adjust the molecular weight.

The reaction is carried out in a solvent or without solvent. The solvent used is not particularly limited so long as it does not react with the diisocyanate compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, or halogenated hydrocarbon solvent such as methylene chloride, ethylene dichloride or chlorobenzene.

The reaction temperature of this reaction is usually at least 0° C. and at most 100° C., preferably at least 20° C. and at most 80° C. If it is less than 0° C., the reaction will take too long, and if it exceeds 100° C., impurities tend to increase and the purity of the desired compound will decrease.

The reaction time in the reaction varies depending upon the reaction temperature and is usually from about 1 hour to about 30 hours. It is preferably from 5 hours to 10 hours.

After completion of the reaction, as the case requires, unreacted raw material, the solvent and the catalyst are removed by washing, by vacuum distillation, by filtration or the like alone or in combination. In a case where the product is a solid, crystals precipitated during concentration may be recrystallized from a poor solvent such as an alcohol or hexane, or dried up as they are, whereby crystals can be obtained. In a case where the formed product is a liquid, it is dried up as it is, followed by purification such as distillation as the case requires, to obtain an oligomer of a 9,10-bis(substituted oxy)anthracene compound.

Further, as shown in the following reaction scheme 4, in a case where a dihalogen compound or a diol compound is used as the bifunctional compound, an oligomer of a 9,10-bis(substituted oxy)anthracene compound having repeating units of the formula (4) can be obtained.

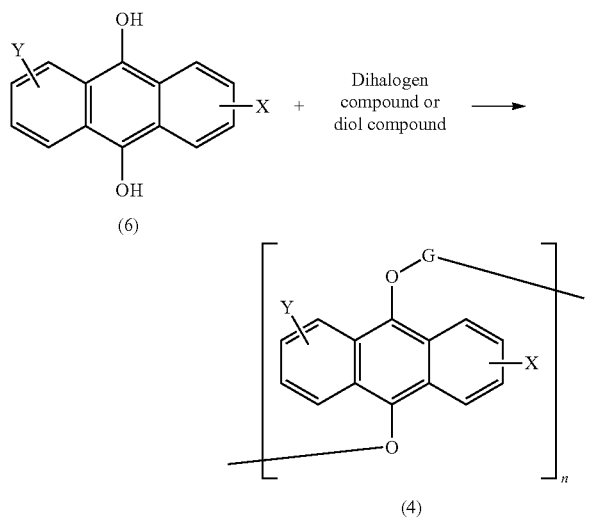

In the reaction scheme 4, n represents a repetition number and is from 2 to 50, each of X and Y which may be the same or different, is a hydrogen atom, a $C_{1-8}$ alkyl group or a halogen atom, G is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

The dihalogen compound may, for example, be dibromomethane, dibromoethane, dibromopropane, dibromobutane, dibromohexane, dibromoheptane, dibromooctane, dibromononane, dibromodecane or 1,5-dibromo-3-methylpentane. The diol compound may, for example, be ethylene glycol, propylene glycol, butanediol, neopentyl glycol, dihydroxybenzene or dihydroxynaphthalene.

In the reaction with the dihalogen compound, a basic compound is required. The basic compound used for the reaction with the dihalogen compound may, for example, be sodium hydride, potassium hydride, sodium hydroxide, potassium hydroxide, sodium carbonate, potassium carbonate, sodium bicarbonate, lithium hexamethyldisilazide, lithium diisopropylamide, triethylamine, tributylamine, trihexylamine, dimethylamine, diethylamine, dipropylamine, dibutylamine, cyclohexylamine, pyridine, piperidine, γ-picoline or lutidine. In the reaction with the diol, the reaction rate will increase and efficient production will be possible by using a catalyst. The catalyst to be used for the reaction with the diol compound may, for example, be a mineral acid (sulfuric acid or hydrochloric acid), an organic acid (methanesulfonic acid or p-toluenesulfonic acid), a base acid (boron fluoride etherate, aluminum trichloride, titanium tetrachloride, iron trichloride or zinc dichloride), a solid acid catalyst (manufactured by Futamura Chemical Co., Ltd.), Amberlist (manufactured by ORGANO CORPORATION), Nafion (manufactured by DuPont), a titanium tetraalkoxide compound (titanium tetraisopropoxide, titanium tetra-n-butoxide or titanium tetramethoxide) or an organic tin compound (dibutyltin dilaurate or dibutyltin oxide).

The amount of the basic compound added is preferably at least 2.0 molar times and less than 5.0 molar times, more preferably at least 2.2 molar times and less than 3.0 molar times, the 9,10-dihydroxyanthracene compound. If it is less than 2.0 molar times, the reaction will not be completed, and if it is at least 5.0 molar times, side reaction may occur, and the yield and the purity will decrease.

The amount of the catalyst added is preferably at least 0.01 mol % and less than 20 mol %, more preferably at least 0.1 mol % and less than 10 mol %, to the 9,10-dihydroxyanthracene compound. If it is less than 0.01 mol %, the reaction rate will be low, and if it is at least 20 mol %, the purity of the formed product will decrease.

In a case where the 9,10-dihydroxyanthracene compound is dissolved in an aqueous solution of an inorganic base and is reacted with the dihalogen compound or the diol compound, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate will be low, and if it is at least 1.0 molar times, the purity of the product will decrease.

The amount of the dihalogen compound or the diol compound added to the 9,10-dihydroxyanthracene compound represented by the formula (6) is at least 0.5 molar times and at most 5.0 molar times, preferably at least 1.0 molar times and at most 3.0 molar times. If it is less than 0.5 molar times, the average molecular weight tends to be low, and the migration property cannot be suppressed, and further, an unreacted 9,10-dihydroxyanthracene compound will remain in the product, thus lowering the purity. Further, if it exceeds 5.0 molar times, the average molecular weight tends to be low, and the migration property cannot be suppressed, and in addition, an unreacted dihalogen compound or diol compound will remain in the product, thus lowering the purity.

Further, as the molar ratio of the dihalogen compound or the diol compound to the 9,10-dihydroxyanthracene compound represented by the formula (6) is closer to 1, the average molecular weight tends to be too high, the mobility of the molecules will be lower, and the sensitizing performance may decrease. In such a case, a monohalogen compound or a monool compound may be added in a small amount to adjust the molecular weight.

The reaction is carried out in a solvent or without solvent. The solvent used is not particularly limited so long as it does not react with the dihalogen compound or the diol compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, a halogenated hydrocarbon solvent such as methylene chloride, ethylene dichloride or chlorobenzene, or water.

The reaction temperature of this reaction is, in the case of the reaction with the dihalogen compound, usually at least 0° C. and at most 200° C., preferably at least 50° C. and at most 150° C. If it is less than 0° C., the reaction will take too long, and if it exceeds 200° C., impurities tend to increase and the purity of the desired compound will decrease. In the case of the reaction with the diol compound, the reaction temperature is usually at least 50° C. and at most 250° C., preferably at least 100° C. and less than 200° C. If it is less than 50° C., the reaction will take too long, and if it exceeds 250° C., impurities tend to increase, and the purity of the desired compound will decrease.

The reaction time in the reaction varies depending upon the reaction temperature and is usually from about 1 hour to about 30 hours. It is preferably from 1 hour to 10 hours.

After completion of the reaction, as the case requires, unreacted raw material, the solvent and the catalyst are removed by washing, by vacuum distillation, by filtration or the like alone or in combination. In a case where the product is a solid, crystals precipitated after the reaction may be subjected to filtration and dried, or dried up as they are, whereby crystals can be obtained. In a case where the formed product is a liquid, it is dried up as it is, followed by purification such as distillation as the case requires, to obtain an oligomer of a 9,10-bis(substituted oxy)anthracene compound.

Further, in a case where a diglycidyl compound is used as the bifunctional compound as shown in the following reaction scheme 5, an oligomer of a 9,10-bis(substituted oxy) anthracene compound having repeating units of the formula (5) is obtained.

Reaction scheme 5

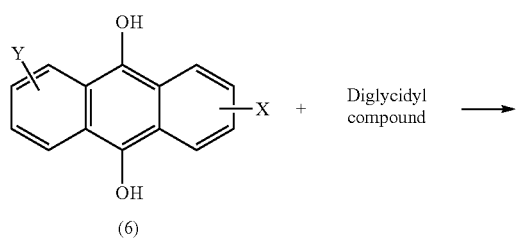

(6)

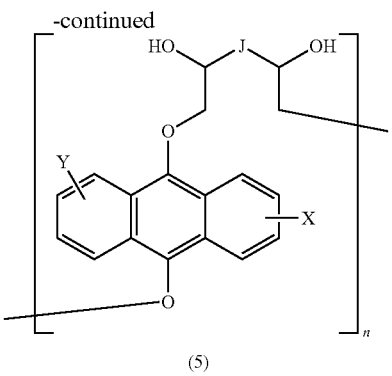

(5)

In the reaction scheme 5, n represents a repetition number and is from 2 to 50, each of X and Y which may be the same or different, is a hydrogen atom, a $C_{1-8}$ alkyl group or a halogen atom, J is a $C_{1-20}$ alkylene group or a $C_{6-20}$ arylene group, the alkylene group may contain an oxygen atom, a nitrogen atom, a sulfur atom, a benzene ring or a naphthalene ring, the benzene ring and the naphthalene ring may be substituted by an alkyl group, the arylene group may have a substituent, and a plurality of rings may be bonded by an alkylene group, an oxygen atom, a nitrogen atom or a sulfur atom.

The diglycidyl compound may be any of an aliphatic diglycidyl ether compound, an alicyclic diglycidyl ether compound and an aromatic diglycidyl ether compound. The aliphatic diglycidyl ether compound may, for example, be ethylene glycol diglycidyl ether, neopentyl glycol diglycidyl ether, diethylene glycol diglycidyl ether, 1,4-butanediol diglycidyl ether or 1,6-hexanediol diglycidyl ether, the alicyclic diglycidyl ether compound may, for example, be hydrogenated bisphenol A diglycidyl ether or hydrogenated bisphenol F diglycidyl ether, and the aromatic diglycidyl ether may, for example, be bisphenol A diglycidyl ether, bisphenol F diglycidyl ether or hydroquinone diglycidyl ether.

In the reaction with the diglycidyl compound, a basic compound is required. The basic compound used for the reaction with the diglycidyl compound may, for example, be sodium hydride, potassium hydride, sodium hydroxide, potassium hydroxide, sodium carbonate, potassium carbonate, sodium bicarbonate, lithium hexamethyldisilazide, lithium diisopropylamide, triethylamine, tributylamine, trihexylamine, dimethylamine, diethylamine, dipropylamine, dibutylamine, cyclohexylamine, pyridine, piperidine, γ-picoline or lutidine.

The amount of the basic compound added is preferably at least 2.0 molar times and less than 5.0 molar times, more preferably at least 2.2 molar times and less than 3.0 molar times, the 9,10-dihydroxyanthracene compound. If it is less than 2.0 molar times, the reaction will not be completed, and if it is at least 5.0 molar times, a side reaction may occur, and the yield and the purity will decrease.

In a case where the 9,10-dihydroxyanthracene compound is dissolved in an aqueous solution of an inorganic base and is reacted with the diglycidyl compound, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate will be low, and if it is at least 1.0 molar times, the purity of the product will decrease.

The amount of the diglycidyl compound added to the 9,10-dihydroxyanthracene compound represented by the formula (6) is at least 0.5 molar times and at most 5.0 molar times, preferably at least 1.0 molar times and at most 3.0 molar times. If it is less than 0.5 molar times, the average molecular weight tends to be low, and the migration property cannot be suppressed, and further, an unreacted 9,10-dihydroxyanthracene compound will remain in the product, thus lowering the purity. Further, if it exceeds 5.0 molar times, the average molecular weight tends to be low, and the migration property cannot be suppressed, and in addition, an unreacted diglycidyl compound will remain in the product, thus lowering the purity.

Further, as the molar ratio of the diglycidyl compound to the 9,10-dihydroxyanthracene compound represented by the formula (6) is closer to 1, the average molecular weight tends to be too high, the mobility of the molecules will be lower, and the sensitizing performance may decrease. In such a case, a monoglycidyl compound may be added in a small amount to adjust the molecular weight.

The reaction is carried out in a solvent or without solvent. The solvent used is not particularly limited so long as it does not react with the diglycidyl compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, a halogenated hydrocarbon solvent such as methylene chloride, ethylene dichloride or chlorobenzene, or water.

The reaction temperature of this reaction is usually at least 0° C. and at most 200° C., preferably at least 50° C. and at most 150° C. If it is less than 0° C., the reaction will take too long, and if it exceeds 200° C., impurities tend to increase and the purity of the desired compound will decrease.

The reaction time in the reaction varies depending upon the reaction temperature and is usually from about 1 hour to about 30 hours. It is preferably from 3 hours to 10 hours.

After completion of the reaction, as the case requires, unreacted raw material, the solvent and the catalyst are removed by washing, by vacuum distillation, by filtration or the like alone or in combination. In a case where the product is a solid, crystals precipitated during concentration may be recrystallized from a poor solvent such as an alcohol or hexane, or dried up as they are, whereby crystals can be obtained. In a case where the formed product is a liquid, it is dried up as it is, followed by purification such as distillation as the case requires, to obtain an oligomer of a 9,10-bis(substituted oxy)anthracene compound.

(Photopolymerization Sensitizer)

The oligomer of a 9,10-bus(substituted oxy)anthracene compound having repeating units represented by the formula (1) of the present invention thus obtained may be used as a photocationic polymerization sensitizer or a photoradical polymerization sensitizer when a photocationic polymerizable compound or a photoradical polymerizable compound is polymerized in the presence of a photopolymerization initiator.

Further, the photopolymerization sensitizer containing the oligomer of a 9,10-bis(substituted oxy)anthracene compound having repeating units represented by the formula (1) of the present invention contains the oligomer of a 9,10-bis (substituted oxy)anthracene compound as an effective component, and it may consist of the oligomer of a 9,10-bis (substituted oxy)anthracene compound or may contain a photopolymerization sensitizer or the like other than the oligomer of a 9,10-bis(substituted oxy)anthracene compound within a range not to impair the effects of the present invention.

The photopolymerization sensitizer other than the oligomer of a 9,10-bis(substituted oxy)anthracene compound may, for example, be an anthracene compound (9,10-bisoctanoyloxyanthracene or 9,10-bisnonanoyloxyanthracene), a thioxanthone compound (such as 1-isopropylthioxanthone or 2,4-diethylthioxanthone), a naphthalene compound (such as 1,4-diethoxynaphthalene, 1,4-dimethoxynaphthalene, 1,4-dihydroxynaphthalene or 4-methoxy-1-naphtol) or an amine compound (such as methyl diethylaminobenzoate).

The 9,10-dihydroxyanthracene compound represented by the formula (6) which is a raw material for preparation of the oligomer of a 9,10-bis(substituted oxy)anthracene compound having repeating units represented by the formula (1) of the present invention is also a compound having an effect as a photopolymerization sensitizer. However, by the compound being oligomerized by the bifunctional compound, the migration resistance is remarkably improved. Further, the oligomer of a 9,10-bis(substituted oxy)anthracene compound having repeating units represented by the formula (1) of the present invention, in which the bivalent substituent represented by A is directly bonded to the anthracene ring via an oxygen atom, and which has a high anthracene ring concentration in the oligomer, is a compound having a high effect as a photopolymerization sensitizer.

The proportion of the photopolymerization sensitizer other than the oligomer of a 9,10-bis(substituted oxy)anthracene compound added to the oligomer of a 9,10-bis (substituted oxy)anthracene compound is not particularly limited and is at least 0.1 time by weight and at most 10 times by weight to the oligomer of a 9,10-bis(substituted oxy)anthracene compound.

(Photopolymerization Initiator)

The photopolymerization initiator is preferably an onium salt, a benzyl methyl ketal or α-hydroxyalkylphenone polymerization initiator. As the onium salt, usually an iodonium salt or a sulfonium salt is used. The iodonium salt may, for example, be 4-isobutylphenyl-4'-methylphenyl iodonium hexafluorophosphate, bis(dodecylphenyl)iodonium hexamethoxyantimonate, 4-isopropylphenyl-4'-methylphenyliodonium tetrakis pentamethoxyphenyl borate, or 4-isopropylphenyl-4'-methylphenyliodonium tetrakis pentafluorophenyl borate, and for example, Irgacure 250 manufactured by BASF (registered trademark), Rhodorsil 2074 manufactured by Rhodia Co., Ltd. (registered trademark) or IK-1 manufactured by San Apro Co., Ltd. may be used. Further, the sulfonium salt may, for example, be S,S,S',S'-tetraphenyl-S,S'-(4,4'-thiodiphenyl)disulfonium bishexamethoxyphosphate, diphenyl-4-phenylthiophenylsulfonium hexamethoxyphosphate or triphenylsulfonium hexamethoxyphosphate, and for example, CPI-100P, CPI101P or CPI-200K manufactured by Daicel Corporation, Irgacure 270 manufactured by BASF, or UVI6992 manufactured by Dow Chemical, may be used. Such a photopolymerization initiator may be used alone or in combination of two or more.

Further, the compound of the present invention has an excellent photopolymerization sensitizing effect also for a radical polymerization initiator such as a benzyl methyl ketal or α-hydroxyalkylphenone polymerization initiator.

As specific compounds, the benzyl methyl ketal radical polymerization initiator may, for example, be 2,2-dimethoxy-1,2-diphenylethan-1-one (tradename "Irgacure 651" manufactured by BASF), and the α-hydroxyalkylphenone radical polymerization initiator may be 2-hydroxy-2-methyl-1-phenylpropan-1-one (tradename "DAROCUR 1173" manufactured by BASF, 1-hydroxycyclohexyl phenyl ketone (tradename "Irgacure 184" manufactured by BASF), 1-[4-(2-hydroxyethoxy)-phenyl]-2-hydroxy-2-methyl-1-propan-1-one (tradename "Irgacure 2959" manufactured by BASF) or 2-hydroxy-1-{4-[4-(2-hydroxy-2-methylpropionyl)-benzyl]phenyl}-2-methyl-1-one (tradename "Irgacure 127" manufactured by BASF).

Particularly preferred is 2,2-dimethoxy-1,2-diphenylethan-1-one (tradename "Irgacure 651" manufactured by BASF) which is a benzyl methyl ketal radical polymerization initiator, or 2-hydroxy-2-methyl-1-phenylpropan-1-one (tradename "DAROCUR 1173" manufactured by BASF) or 1-hydroxycyclohexyl phenyl ketone (tradename "Irgacure 184" manufactured by BASF) which is an α-hydroxyalkylphenone radical photopolymerization initiator.

Further, it is possible to use acetophenone, 2-hydroxy-2-phenylacetophenone, 2-ethoxy-2-phenylacetophenone, 2-methoxy-2-phenylacetophenone, 2-isopropoxy-2-phenylacetophenone or 2-isobutoxy-2-phenylacetophenone which is an acetophenone radical polymerization initiator, benzyl or 4,4'-dimethoxybenzyl which is a benzyl radical polymerization initiator, or 2-ethylanthraquinone, 2-t-butylanthraquinone, 2-phenoxyanthraquinone, 2-(phenylthio)anthraquinone or 2-(hydroxyethylthio)anthraquinone which is an anthraquinone radical polymerization initiator.

Among the above exemplified photopolymerization initiators, an onium salt is particularly preferred. One of characteristics of the oligomer of a 9,10-bis(substituted oxy)anthracene compound of the present invention is a photopolymerization sensitizing effect not only on an iodonium salt but also on a sulfonium salt as the onium salt.

The amount of the photopolymerization sensitizer containing the oligomer of a 9,10-bis(substituted oxy)anthracene compound having repeating units represented by the formula (1) of the present invention used to the photopolymerization initiator is not particularly limited, and is usually within a range of at least 5 wt % and at most 100 wt %, preferably at least 10 wt % and at most 50 wt % to the photopolymerization initiator. If the amount of the photopolymerization sensitizer used is less than 5 wt %, photopolymerization of a photopolymerizable compound will take too long, and on the other hand, even if it exceeds 100 wt %, no further effect will be obtained.

(Photopolymerization Initiator Composition)

The photopolymerization sensitizer containing the oligomer of a 9,10-bis(substituted oxy)anthracene compound having repeating units represented by the formula (1) of the present invention may be directly added to a photopolymerizable compound, or it may be preliminarily blended with a photopolymerization initiator to prepare a photopolymerization initiator composition, which is added to a photopolymerizable compound. That is, the photopolymerization initiator composition of the present invention is a composition comprising at least the photopolymerization sensitizer containing the oligomer of a 9,10-bis(substituted oxy)anthracene compound represented by the formula (1) and an onium salt as a photopolymerization initiator.

(Photopolymerizable Composition)

Further, by blending the photopolymerization initiator composition and a photopolymerizable compound, a photopolymerizable composition may be prepared. The photopolymerizable composition of the present invention is a composition comprising the photopolymerizable initiator composition comprising the photopolymerization sensitizer containing the oligomer of a 9,10-bis(substituted oxy)anthracene compound having repeating units represented by the formula (1) and a photopolymerization initiator of the present invention, and a photoradical polymerizable compound or a photocationic polymerizable compound. The photopolymerization sensitizer containing the oligomer of a 9,10-bis(substituted oxy)anthracene compound having repeating units represented by the formula (1) of the present invention, and the photopolymerization initiator, may be separately added to a photoradical polymerizable compound or a photocationic polymerizable compound and forms a photopolymerization initiator composition in the photoradical polymerizable compound or the photocationic polymerizable compound.

The photoradical polymerizable compound may, for example, be an organic compound having a double bond such as styrene, vinyl acetate, acrylic acid, methacrylic acid, acrylonitrile, methacrylonitrile, acrylamide, acrylic acid ester or methacrylic acid ester. Among such radical polymerizable compounds, in view of the film forming performance, etc., preferred is an acrylic acid ester or a methacrylic acid ester (hereinafter both will generally be referred to as a (meth)acrylic acid ester). The (meth)acrylic acid ester may, for example, be methyl acrylate, butyl acrylate, cyclohexyl acrylate, 2-ethylhexyl acrylate, 2-hydroxyethyl acrylate, isobornyl acrylate, methyl methacrylate, butyl methacrylate, cyclohexyl methacrylate, tetraethylene glycol diacrylate, trimethylolpropane triacrylate, pentaerythritol triacrylate, tricyclo[5,2,1,02,6]decanedimethanol diacrylate, isobornyl methacrylate, epoxy acrylate, urethane acrylate, polyester acrylate, polybutadiene acrylate, polyol acrylate, polyether acrylate, silicone resin acrylate or imide acrylate. Such a photoradical polymerizable compound may be used alone or as a mixture of two or more.

The photocationic polymerizable compound may, for example, be an epoxy compound or a vinyl ether. As the epoxy compound, commonly, an alicyclic epoxy compound, an epoxy-modified silicone or an aromatic glycidyl ether may, for example, be mentioned. The alicyclic epoxy compound may, for example, be 3,4-epoxycyclohexylmethyl-3,4-epoxycyclohexanecarboxylate (manufactured by Daicel Corporation, tradename: CELLOXIDE 2021P, registered trademark) or bis(3,4-epoxycyclohexyl)adipate. The epoxy-modified silicone may, for example, be UV-9300 manufactured by GE Toshiba Silicones. The aromatic glycidyl compound may, for example, be 2,2'-bis(4-glycidyloxyphenyl)propane. The vinyl ether may, for example, be methyl vinyl ether, ethyl vinyl ether, isobutyl vinyl ether or 2-ethylhexyl vinyl ether. Such a photocationic polymerizable compound may be used alone or as a mixture of two or more.

In the photopolymerizable composition of the present invention, the amount of the photopolymerizable initiator composition used is within a range of at least 0.005 wt % and at most 10 wt %, preferably at least 0.025 wt % and at most 5 wt %, to the photopolymerizable composition. If it is less than 0.005 wt %, photopolymerization of the photopolymerizable composition will take long, and on the other hand, if it exceeds 10 wt %, the hardness of a photo-cured product obtained by photopolymerization will be low, and physical properties of the cured product will deteriorate.

The photopolymerizable composition of the present invention may contain, within a range not to impair the effects of the present invention, resin additives such as a diluent, a coloring agent, an organic or inorganic filler, a levelling agent, a surfactant, an anti-foaming agent, a thickener, a flame retardant, an antioxidant, a stabilizer, a lubricant or a plasticizer.

(Photo-Cured Product)

The photo-cured product of the present invention is obtained by irradiating the photopolymerizable composition with light and polymerizing it. In a case where the photopolymerizable composition is irradiated with light and polymerized to be photo-cured, the photopolymerizable composition may be formed into a film-form and photo-cured, or may be formed in a block and photo-cured. In a case where it is formed into a film and photo-cured, the photopolymerizable composition which is in a liquid form is applied to a substrate such as a polyester film to a film thickness of from 5 to 300 micron by a bar coater or the like. Otherwise, it may be applied with a thinner or thicker film thickness by spin coating method or screen printing method.

A coating film formed of the photopolymerizable composition thus prepared is irradiated with ultraviolet rays within a wavelength range of from 250 to 500 nm at an intensity of from about 1 to about 1,000 mW/cm$^2$ to obtain a photo-cured product. The light source used may, for example, be a high pressure mercury lamp, an ultrahigh pressure mercury lamp, a metal halide lamp, a xenon lamp, a gallium-doped lamp, black light, a 405 nm ultraviolet LED, a 395 nm ultraviolet LED, a 385 nm ultraviolet LED, a 365 nm ultraviolet LED, a blue LED, a white LED, or D bulb or V bulb manufactured by FUSION. Natural light such as sunlight may be used.

(Photo DSC Measurement)

In the present invention, as a means to quantitatively evaluate the photopolymerization rate of the photopolymerizable composition under irradiation with light, photo DSC measurement is employed. According to this means, while a sample is directly irradiated with light, the heating value accompanying curing can be continuously and easily measured. When a sample set to a photo DSC measurement apparatus is irradiated with light, photo-curing reaction starts, and heat generation is measured. The baseline of a DSC curve which is horizontal before photo-curing shifts toward the exothermic side, and after the reaction is completed, it returns to the original baseline position. The heating value can be obtained from the intensity of the peak of the DSC curve. That is, by irradiating the photopolymerizable composition with light and measuring and comparing the heating value per 1 mg, the progress of the polymerization can be evaluated.

(Judgement of Migration Resistance)

As a method to judge whether the photopolymerizable sensitizer contained in the photopolymerization composition of the present invention migrates to the film or the like or not, a photopolymerizable composition comprising the photopolymerization sensitizer is applied to a thin film, which is covered with a polyethylene film and stored at a constant temperature (26° C.) for a constant period, and then the polyethylene film is peeled, and whether the photopolymerization sensitizer migrates to the polyethylene film or not is evaluated, to judge the migration resistance. The peeled polyethylene film is washed with acetone to remove the composition on the surface and dried, an UV spectrum of the polyethylene film is measured, and an increase of the absorption intensity resulting from the photopolymerization sensitizer is examined to measure the migration resistance. For this measurement, an UV/visible spectrophotometer (manufactured by SHIMADZU CORPORATION, model: UV2200) is used. For quantitative comparison with 9,10-dibutoxyanthracene which is a compound in Comparative Examples, the obtained absorbance is calculated as an absorbance of 9,10-dibutoxyanthracene. For calculation, absorbances of the compound of the present invention and 9,10-dibutoxyanthracene at 260 nm are measured by the ultraviolet/visible spectrophotometer, and the respective molar absorption coefficients are calculated from the absorbances and the molar concentrations, and calculation is made using their ratio.

EXAMPLES

Now, the present invention will be described in further detail with reference to Examples. However, Examples are merely exemplified as examples. That is, the following Examples are not exhaustive nor intended to restrict the present invention as described. Accordingly, the present invention is by no means restricted to the following Examples within a range not to exceed the scope of the present invention. Further, unless otherwise specified, all the parts and percentages are based on the weight.

Formed products were confirmed based on measurements by the following equipment.

(1) Infrared (IR) spectrophotometer: manufactured by Thermo Fisher Scientific K.K., model is 50 FT-IR (2) Nuclear magnetic resonance (NMR) apparatus: manufactured by JEOL Ltd., model ESC-400

(3) Molecular weight distribution: GPC, manufactured by JASO Corporation, 2000 series Examples for Preparation of Compounds of the Present Invention (Example 1) Oligomer Obtained by Reaction of 9,10-dihydroxyanthracene and Adipic Acid Chloride [Compound No. 2-6]

In a nitrogen atmosphere, into a 200 ml four-necked flask equipped with a stirring blade, 30 g (150 mmol) of a 20% NaOH aqueous solution, 28.7 g (24 mmol as anthraquinone) of a sodium salt 17.4% aqueous solution of 9,10-dihydroxyanthracene, 0.8 g (1.2 mmol) of a 50% aqueous solution of tetrabutylammonium bromide and 50 g of toluene as a reaction solvent were charged. 13.2 g (72 mmol) of adipic acid chloride was added dropwise over a period of 3 hours so that the internal temperature would not exceed 20° C. After completion of the dropwise addition, stirring was continued for 30 minutes, and precipitated crystals were subjected to vacuum filtration, washed with toluene and deionized water and vacuum dried to obtain 8.4 g of an oligomer obtained by reaction of 9,10-dihydroxyanthracene and adipic acid chloride (pale orange crystals).

(1) IR (cm$^{-1}$) 2935, 1754, 1573, 1362, 1248, 1110, 908, 756, 733, 609

(2) $^1$H-NMR (400 MHz, DMSO-D$_6$): δ=0.91-0.94 (m), 1.29-1.33 (m), 1.47-1.50 (m), 1.69-1.75 (m), 1.81-1.85 (m), 2.03-2.08 (m), 2.17-2.19 (m), 2.32-2.35 (m), 3.06-3.09 (m), 7.57-7.64 (m), 7.94-7.95 (m), 8.04-8.10 (m), 8.21-8.23 (m)

(3) Molecular weight distribution n=2 to 20

(Example 2) Oligomer Obtained by Reaction of 9,10-dihydroxyanthracene and Sebacoyl Chloride [Compound No. 2-10]

In a nitrogen atmosphere, into a 200 ml four-necked flask equipped with a stirring blade, 30 g (150 mmol) of a 20% NaOH aqueous solution, 28.7 g (24 mmol as anthraquinone) of a sodium salt 17.4% aqueous solution of 9,10-dihydroxy-anthracene, 0.8 g (1.2 mmol) of a 50% aqueous solution of tetrabutylammonium bromide and 50 g of toluene as a reaction solvent were charged. 17.2 g (72 mmol) of sebacoyl chloride was added dropwise over a period of 3 hours so that the internal temperature would not exceed 20° C. After completion of the dropwise addition, stirring was continued for 1 hour, and precipitated crystals were subjected to vacuum filtration, washed with deionized water and methanol and vacuum dried to obtain 5.9 g of an oligomer obtained by reaction of 9,10-dihydroxyanthracene and adipid acid chloride (pale yellow crystals).

(1) IR (cm$^{-1}$) 2927, 2851, 1751, 1703, 1353, 1171, 1102, 755, 736, 609.

(2) $^1$H-NMR (400 MHz, DMSO-D$_6$): δ=1.23 (s), 1.32-1.83 (m), 2.13-2.19 (m), 2.25-2.32 (m), 3.03-3.06 (m), 3.56 (s), 7.61-7.63 (m), 7.93-7.95 (m), 8.02-8.04 (m), 8.21-8.23 (m)

(3) Molecular weight distribution n=2 to 7

(Example 3) Oligomer Obtained by Reaction of 2-Methyl-9,10-dihydroxyanthracene and Adipic Acid Chloride [Compound No. 2-17]

In a nitrogen atmosphere, into a 100 ml four-necked flask equipped with a stirring blade, 35.6 g (140 mmol) of a 16% NaOH aqueous solution, 2.0 g (9 mmol) of 2-methyl-9,10-anthraquinone and 3.9 g (36 mmol) of thiourea dioxide were charged. The mixture was stirred at from 50 to 60° C. for one hour to prepare a sodium salt aqueous solution of 2-methyl-9,10-dihydroxyanthracene. The aqueous solution was cooled to 20° C. or below, and 0.3 g (0.4 mmol) of a 50% aqueous solution of tetrabutylammonium bromide and 20 g of toluene as a reaction solvent were charged. 4.9 g (27 mmol) of adipic acid chloride was added dropwise over a period of 3 hours so that the internal temperature would not exceed 20° C. After completion of the dropwise addition, stirring was continued for one hour, and precipitated crystals were subjected to vacuum filtration, washed with deionized water and methanol and vacuum dried to obtain 3.0 g of an oligomer obtained by reaction of 2-methyl-9,10-dihydroxyanthracene and adipic acid chloride (orange crystals).

(1) IR (cm$^{-1}$) 2943, 1754, 1367, 1350, 1110, 914, 811, 744, 711.

(2) $^1$H-NMR (400 MHz, DMSO-D$_6$): δ=0.91-0.94 (m), 1.29-1.31 (m), 1.69-1.73 (m), 1.80-1.86 (m), 2.06 (s), 2.29 (s), 7.15-7.24 (m), 7.41 (s), 7.56 (s), 7.74-7.81 (m), 7.91-8.05 (m), 8.11-8.13 (m), 8.20-8.21 (m).

(3) Molecular weight distribution n=2 to 11

(Example 4) Oligomer Obtained by Reaction of 2-ethyl-9,10-dihydroxyanthracene and Adipic Acid Chloride [Compound No. 2-23]

In a nitrogen atmosphere, into a 100 ml four-necked flask equipped with a stirring blade, 35.4 g (135 mmol) of a 15% NaOH aqueous solution, 2.0 g (8.5 mmol) of 2-ethyl-9,10-anthraquinone and 3.7 g (34 mmol) of thiourea dioxide were charged. The mixture was stirred at from 50 to 60° C. for one hour to prepare a sodium salt aqueous solution of 2-ethyl-9,10-dihydroxyanthracene. The aqueous solution was cooled to 20° C. or below, and 0.3 g (0.4 mmol) of a 50% aqueous solution of tetrabutylammonium bromide and 20 g of toluene as a reaction solvent were charged. 4.6 g (25 mmol) of adipic acid chloride was added dropwise over a period of 3 hours so that the internal temperature would not exceed 20° C. After completion of the dropwise addition, stirring was continued for one hour, and precipitated crystals were subjected to vacuum filtration, washed with deionized water and methanol and vacuum dried to obtain 2.7 g of an oligomer obtained by reaction of 2-ethyl-9,10-dihydroxyanthracene and adipic acid chloride (orange crystals).

(1) IR (cm$^{-1}$) 2931, 1748, 1352, 1110, 1038, 815, 739, 592.

(2) $^1$H-NMR (400 MHz, DMSO-D$_6$): δ=0.90-0.94 (m), 1.17-1.18 (m), 1.24-1.32 (m), 1.48-1.55 (m), 1.68-1.73 (m), 1.80-1.84 (m), 2.06 (s), 2.25 (s), 2.29 (s), 2.75-2.83 (m), 3.05 (s), 3.12-3.40 (m), 7.45 (s), 7.56 (s), 7.74-7.78 (m), 7.91-8.05 (m), 8.13-8.15 (m), 8.19-8.22 (m).

(3) Molecular weight distribution n=2 to 22

(Example 5) Oligomer Obtained by Reaction of 2-ethyl-9,10-dihydroxyanthracene and Sebacoyl Chloride [Compound No. 2-25]

In a nitrogen atmosphere, into a 100 ml four-necked flask equipped with a stirring blade, 35.4 g (135 mmol) of a 15% NaOH aqueous solution, 2.0 g (8.5 mmol) of 2-ethyl-9,10-anthraquinone and 3.7 g (34 mmol) of thiourea dioxide were charged. The mixture was stirred at from 50 to 60° C. for one hour to prepare a sodium salt aqueous solution of 2-ethyl-9,10-dihydroxyanthracene. The aqueous solution was cooled to 20° C. or below, and 0.3 g (0.4 mmol) of a 50% aqueous solution of tetrabutylammonium bromide and 20 g of toluene as a reaction solvent were charged. 6.1 g (25 mmol) of sebacoyl chloride was added dropwise over a period of 3 hours so that the internal temperature would not exceed 20° C. After completion of the dropwise addition, stirring was continued for one hour, and precipitated crystals were subjected to vacuum filtration, washed with deionized water and methanol and vacuum dried to obtain 3.5 g of an oligomer obtained by reaction of 2-ethyl-9,10-dihydroxyanthracene and sebacoyl chloride (yellow crystals).

(1) IR (cm$^{-1}$) 2928, 2855, 1754, 1349, 1150, 1099, 1040, 815, 757, 733.

(2) $^1$H-NMR (400 MHz, DMSO-D$_6$): δ=0.91-0.94 (m), 1.23-1.49 (m), 1.85 (s), 2.00-2.06 (m), 7.59-7.99 (m).

(3) Molecular weight distribution n=2 to 22

(Example 6) Oligomer Obtained by Reaction of 9,10-dihydroxyanthracene and Isophorone Diisocyanate [Compound No. 3-6]

In a nitrogen atmosphere, into a 50 ml four-necked flask in which a stirrer was put, 1 g (4.8 mmol) of 9,10-dihydroxyanthracene, 1.6 g (7.1 mmol) of isophorone diisocyanate, 0.05 g (0.5 mmol) of triethylamine and 20 g of tetrahydrofuran as a reaction solvent were charged. The mixture was stirred at room temperature for 2 hours and at 65° C. for 2 hours, the reaction was quenched with 1 ml of methanol, and the reaction mixture was cooled to room temperature. Insoluble matters were removed by filtration, and the filtrate was concentrated to dryness to obtain 2.4 g of an oligomer obtained by reaction of 9,10-dihydroxyanthracene and isophorone diisocyanate (orange crystals).

(1) IR (cm$^{-1}$) 3310, 2949, 1698, 1526, 1232, 1042, 696.
(2) $^1$H-NMR (400 MHz, DMSO-D$_6$): δ=0.75-1.15 (m), 1.39-1.51 (m), 1.73-1.77 (m), 2.69-2.74 (m), 3.08-3.14 (m), 3.48-3.61 (m), 6.95-6.97 (m), 7.08-7.11 (m), 7.61 (s), 7.92-7.96 (m), 8.02-8.04 (m), 8.20-8.23 (m).
(3) Molecular weight distribution n=2 to 9

(Example 7) Oligomer Obtained by Reaction of 9,10-dihydroxyanthracene and 2,4,4-trimethylhexamethylene diisocyanate [Compound No. 3-4]

In a nitrogen atmosphere, into a 50 ml four-necked flask in which a stirrer was put, 1 g (4.8 mmol) of 9,10-dihydroxyanthracene, 1.5 g (7.1 mmol) of 2,4,4-trim ethylhexamethylene diisocyanate, 0.05 g (0.5 mmol) of triethylamine and 20 g of tetrahydrofuran as a reaction solvent were charged. The mixture was stirred at room temperature for 2 hours and at 65° C. for 2 hours, the reaction was quenched with 1 ml of methanol, and the reaction mixture was cooled to room temperature. Insoluble matters were removed by filtration, and the filtrate was concentrated to dryness to obtain 1.7 g of an oligomer obtained by reaction of 9,10-dihydroxyanthracene and 2,4,4-trimethylhexamethylene diisocyanate (yellow crystals).
(1) IR (cm$^{-1}$) 3327, 2954, 2262, 1710, 1522, 1220, 1166, 1041, 621.
(2) $^1$H-NMR (400 MHz, DMSO-D$_6$): δ=0.76-1.03 (m), 1.16-1.60 (m), 2.81-3.22 (m), 7.57 (s), 7.93-7.95 (m), 8.01 (s), 8.20-8.23 (m).
(3) Molecular weight distribution n=2 to 33

(Example 8) Oligomer Obtained by Reaction of 9,10-dihydroxyanthracene and 2,4-toluene diisocyanate [Compound No. 3-7]

In a nitrogen atmosphere, into a 50 ml four-necked flask in which a stirrer was put, 1 g (4.8 mmol) of 9,10-dihydroxyanthracene, 2.1 g (12 mmol) of 2,4-toluene diisocyanate, 0.05 g (0.08 mmol) of dibutyltin dilaurate and 20 g of tetrahydrofuran as a reaction solvent were charged. The mixture was stirred at room temperature for 2 hours and at 65° C. for 2 hours, the reaction was quenched with 1 ml of methanol, and the reaction mixture was cooled to room temperature. The reaction liquid was concentrated to dryness to obtain 3.0 g of an oligomer obtained by reaction of 9,10-dihydroxyanthracene and 2,4-toluene diisocyanate (yellow crystals).
(1) IR (cm$^{-1}$) 3291, 2261, 1715, 1592, 1516, 1367, 1200, 1170, 1060, 990, 869, 869, 810, 737.
(2) $^1$H-NMR (400 MHz, DMSO-D$_6$): δ=0.84 (s), 1.23 (s), 1.73-1.78 (m), 1.96-2.01 (m), 2.08-2.26 (m), 3.57-3.61 (m), 4.23-4.27 (m), 4.75-5.04 (m), 6.35-7.41 (m), 7.64-7.72 (m), 7.93-7.95 (m), 8.14-8.28 (m).
(3) Molecular weight distribution n=2 to 33

(Example 9) Oligomer Obtained by Reaction of 9,10-dihydroxyanthracene and 1,4-dibromobutane [Compound No. 4-4]

Into a 500 ml four-necked flask equipped with a stirring machine and a thermometer, in a nitrogen atmosphere, 25.9 g (120 mmol) of 1,4-dibromobutane, 80.0 g of methyl isobutyl ketone and 3.1 g of a 50% tetrabutylammonium bromide aqueous solution were put. The internal temperature was raised to 92° C., and dropping of 111.7 g (96 mmol as anthraquinone) of a sodium salt 17.9% aqueous solution of 9,10-dihydroxyanthracene was started. The dropwise addition was conducted over a period of 3 hours, and while the internal temperature was maintained, and a forced reaction was conducted for 2 hours. After completion of the reaction, the reaction mixture was cooled to room temperature, and precipitates were subjected to filtration, washed with 20.0 ml of methyl isobutyl ketone and 40.0 ml of pure water twice respectively and dried to obtain 24.8 g of an oligomer obtained by reaction of 9,10-dihydroxyanthracene and 1,4-dibromobutane (yellow crystals).
(1) IR (cm$^{-1}$) 2953, 2881, 1409, 1349, 1065, 1019, 964, 769, 678.
(2) $^1$H-NMR (400 MHz, CDCl$_3$): δ=2.00-2.50 (m), 3.50-3.60 (m), 4.10-4.30 (m), 7.30-7.50 (m), 8.10-8.40 (m)
(3) Molecular weight distribution n=2 to 13

(Example 10) Oligomer Obtained by Reaction of 9,10-dihydroxyanthracene and 1,5-dibromopentane [Compound No. 4-6]

Into a 100 ml four-necked flask equipped with a stirring machine and a thermometer, in a nitrogen atmosphere, 6.9 g (30 mmol) of 1,5-dibromopentane, 20.0 g of methyl isobutyl ketone and 0.8 g of a 50% tetrabutylammonium bromide aqueous solution were put. The internal temperature was raised to 75° C., and dropping of 27.9 g (24 mmol as anthraquinone) of a sodium salt 17.9% aqueous solution of 9,10-dihydroxyanthracene was started. The dropwise addition was conducted over a period of 3 hours, then the internal temperature was raised to 90° C., and a forced reaction was conducted for 2 hours. After completion of the reaction, the reaction mixture was cooled to room temperature, and precipitates were subjected to filtration, washed with 5.0 ml of methyl isobutyl ketone and 10.0 ml of pure water twice respectively and dried to obtain 5.5 g of an oligomer obtained by reaction of 9,10-dihydroxyanthracene and 1,5-dibromopentane (yellow crystals).
(1) IR (cm$^{-1}$) 2938, 2862, 1404, 1373, 1344, 1065, 960, 769, 679.
(2) $^1$H-NMR (400 MHz, CDCl$_3$): δ=1.80-1.90 (m), 2.00-2.30 (m), 3.45-3.55 (m), 4.15-4.35 (m), 7.40-7.55 (m), 8.20-8.40 (m)
(3) Molecular weight distribution n=2 to 22

(Example 11) Oligomer Obtained by Reaction of 9,10-dihydroxyanthracene and 1,8-dibromooctane [Compound No. 4-10]

Into a 100 ml four-necked flask equipped with a stirring machine and a thermometer, in a nitrogen atmosphere, 8.2 g (30 mmol) of 1,8-dibromooctane, 20.0 g of methyl isobutyl ketone and 0.8 g of a 50% tetrabutylammonium bromide aqueous solution were put. The internal temperature was raised to 75° C., and dropping of 27.9 g (24 mmol as anthraquinone) of a sodium salt 17.9% aqueous solution of 9,10-dihydroxyanthracene was started. The dropwise addition was conducted over a period of 3 hours, then the internal temperature was raised to 90° C., and a forced reaction was conducted for 2 hours. After completion of the reaction, the reaction mixture was cooled to room temperature, and precipitates were subjected to filtration, washed with 5.0 ml of methyl isobutyl ketone and 10.0 ml of pure water twice respectively and dried to obtain 9.0 g of an oligomer obtained by reaction of 9,10-dihydroxyanthracene and 1,8-dibromooctane (yellow crystals).

(1) IR (cm$^{-1}$) 2912, 2853, 1463, 1404, 1346, 1065, 1018, 770, 750, 673.
(2) $^1$H-NMR (400 MHz, CDCl$_3$): δ=1.30-2.20 (m), 3.30-3.45 (m), 4.05-4.25 (m), 7.30-7.50 (m), 8.15-8.35 (m)
(3) Molecular weight distribution n=2 to 11

(Example 12) Oligomer Obtained by Reaction of 9,10-dihydroxyanthracene and 1,9-dibromononane [Compound No. 4-11]

Into a 100 ml four-necked flask equipped with a stirring machine and a thermometer, in a nitrogen atmosphere, 8.6 g (30 mmol) of 1,9-dibromononane, 20.0 g of methyl isobutyl ketone and 0.8 g of a 50% tetrabutylammonium bromide aqueous solution were put. The internal temperature was raised to 75° C., and dropping of 27.9 g (24 mmol as anthraquinone) of a sodium salt 17.9% aqueous solution of 9,10-dihydroxyanthracene was started. The dropwise addition was conducted over a period of 3 hours, then the internal temperature was raised to 90° C., and a forced reaction was conducted for 2 hours. After completion of the reaction, the reaction mixture was cooled to room temperature, and an aqueous layer (lower layer) was removed, followed by concentration to dryness to obtain 11.2 g of an oligomer of 9,10-dihydroxyanthracene and 1,9-dibromononane (orange crystals).
(1) IR (cm$^{-1}$) 2926, 2853, 1404, 1348, 1066, 1018, 769, 677.
(2) $^1$H-NMR (400 MHz, CDCl$_3$): δ=0.80-2.30 (m), 3.30-3.45 (m), 4.05-4.25 (m), 7.35-7.55 (m), 8.15-8.40 (m)
(3) Molecular weight distribution n=2 to 31

(Example 13) Oligomer Obtained by Reaction of 9,10-dihydroxyanthracene and 1,10-dibromodecane [Compound No. 4-12]

Into a 100 ml four-necked flask equipped with a stirring machine and a thermometer, in a nitrogen atmosphere, 9.0 g (30 mmol) of 1,10-dibromodecane, 20.0 g of methyl isobutyl ketone and 0.8 g of a 50% tetrabutylammonium bromide aqueous solution were put. The internal temperature was raised to 75° C., and dropping of 27.9 g (24 mmol as anthraquinone) of a sodium salt 17.9% aqueous solution of 9,10-dihydroxyanthracene was started. The dropwise addition was conducted over a period of 3 hours, then the internal temperature was raised to 90° C., and a forced reaction was conducted for 2 hours. After completion of the reaction, the reaction mixture was cooled to room temperature and mixed with 40 ml of methanol to precipitate crystals, the precipitates were collected by filtration and washed with 10.0 ml of pure water and 10.0 ml of methanol twice respectively and dried to obtain 9.7 g of an oligomer obtained by reaction of 9,10-dihydroxyanthracene and 1,10-dibromodecane (yellow crystals).
(1) IR (cm$^{-1}$) 2923, 2851, 1404, 1346, 1064, 1017, 764, 726, 675.
(2) $^1$H-NMR (400 MHz, CDCl$_3$): δ=1.20-2.20 (m), 3.35-3.45 (m), 4.10-4.30 (m), 7.40-7.55 (m), 8.20-8.35 (m)
(3) Molecular weight distribution n=2 to 34

(Example 14) Oligomer Obtained by Reaction of 9,10-dihydroxyanthracene and 1,5-dibromo-3-methylpentane [Compound No. 4-8]

Into a 100 ml four-necked flask equipped with a stirring machine and a thermometer, in a nitrogen atmosphere, 3.7 g (15 mmol) of 1,5-dibromo-3-methylpentane, 10.0 g of methyl isobutyl ketone and 0.4 g of a 50% tetrabutylammonium bromide aqueous solution were put. The internal temperature was raised to 75° C., and dropping of 14.0 g (12 mmol as anthraquinone) of a sodium salt 17.9% aqueous solution of 9,10-dihydroxyanthracene was started. The dropwise addition was conducted over a period of 3 hours, then the internal temperature was raised to 90° C., and a forced reaction was conducted for one hour. After completion of the reaction, the reaction mixture was cooled to room temperature, and precipitates were collected by filtration, washed with 5.0 ml of methyl isobutyl ketone and 10.0 ml of pure water twice respectively and dried to obtain 1.8 g of an oligomer obtained by reaction of 9,10-dihydroxyanthracene and 1,5-dibromo-3-methylpentane (yellow crystals).
(1) IR (cm$^{-1}$) 2957, 2928, 2871, 1457, 1434, 1404, 1343, 1064, 755, 676.
(2) $^1$H-NMR (400 MHz, CDCl$_3$): δ=0.85-1.30 (m), 1.75-2.20 (m), 2.25-2.55 (m), 3.45-3.60 (m), 4.15-4.40 (m), 7.40-7.50 (m), 8.20-8.40 (m)
(3) Molecular weight distribution n=2 to 15

(Example 15) Oligomer Obtained by Reaction of 9,10-dihydroxyanthracene and neopentyl glycol diglycidyl ether [Compound No. 5-2]

Into a 100 ml four-necked flask equipped with a stirring machine and a thermometer, in a nitrogen atmosphere, 6.5 g (30 mmol) of neopentyl glycol diglycidyl ether, 20.0 g of methyl isobutyl ketone and 0.8 g of a 50% tetrabutylammonium bromide aqueous solution were put. The internal temperature was raised to 75° C., and dropping of 27.9 g (24 mmol as anthraquinone) of a sodium salt 17.9% aqueous solution of 9,10-dihydroxyanthracene was started. The dropwise addition was conducted over a period of 30 minutes, followed by reaction for 2 hours, and 6.5 g (30 mmol) of neopentyl glycol diglycidyl ether was further added, followed by reaction further for 5 hours. After completion of the reaction, the reaction mixture was cooled to room temperature, and an aqueous layer (lower layer) was removed. Then, the reaction liquid was subjected to filtration to remove insoluble matters, and the filtrate was concentrated to dryness to obtain 11.8 g of an oligomer obtained by reaction of 9,10-dihydroxyanthracene and neopentyl glycol diglycidyl ether (orange viscous liquid).
(1) IR (cm$^{-1}$) 3398, 2869, 1706, 1458, 1398, 1349, 1100, 1065, 995, 771.
(2) $^1$H-NMR (400 MHz, DMSO-D$_6$): δ=0.65-0.90 (m), 3.00-4.70 (m), 5.25-5.40 (m), 7.35-7.55 (m), 8.20-8.40 (m)
(3) Molecular weight distribution n=2 to 30
(Photo DSC Measurement in System Employing Iodonium Salt as Photopolymerizable Composition and Photopolymerization Initiator)
In this Example, photo DSC measurement was carried out as follows. As a DSC measurement apparatus, XDSC-7200 manufactured by Hitachi High-Technologies Corporation was used, and a photo DSC measurement unit was attached thereto so that DSC measurement could be conducted while applying light. As a light source for light application, LA-410UV manufactured by HAYASHI-REPIC CO., LTD. was used, and a band-pass filter was set so that 405 nm light was taken out and applied to a sample. The light illuminance was 50 mW/cm$^2$. Light from the light source was lead to the upper part of the sample by glass fibers, and the shutter of the light source was trigger controlled so that the DSC measurement could be started simultaneously with initiation of light irradiation. For photo DSC measurement, about 1 mg of a sample was accurately weighed in a measurement aluminum pan, which was put in a DSC measurement part, and the photo DSC unit was attached. Then, the interior of the measurement part was kept in a nitrogen atmosphere and left at rest for 10 minutes, and measurement was started. Measurement was continued for 6 minutes while ordinary light was applied. After the first measurement, measurement was conducted again under the same conditions while the sample was as it was, and a value obtained by subtracting the second measurement result from the first measurement result was taken as the measurement result of the sample. The result was the total heating value per 1 mg of a sample in one minute after light irradiation, unless otherwise specified. The photoreaction may not be completed in one minute depending upon the measurement conditions, however, the total heating value in one minute was employed to compare the reaction behavior at the initial stage of light irradiation. When polymerization of the sample (photopolymerizable composition) occurs accompanying light irradiation, a heat of reaction accompanying the polymerization is generated, and the heat of reaction can be measured by photo DSC. Thus, the degree of progress of polymerization by light irradiation can be measured by photo DSC. In this Example, the total heating value in one minute after light irradiation is measured, and so long as the same polymerizable compound is used, it is considered that the larger the total heating value, the more effectively the polymerization proceeds.

The photopolymerizability evaluation test for a photocationic polymerizable composition employing the oligomer of a 9,10-bis(substituted oxy)anthracene compound of the present invention as a photocationic sensitizer will be described below.

Photo-Curing Rate Evaluation Example 1

100 Parts by weight of 3',4'-epoxycyclohexylmethyl-3,4-epoxycyclohexanecarboxylate (manufactured by Daicel Corporation, tradename: CELLOXIDE 2021P, registered trademark) as a photocationic polymerizable compound, 2 parts by weight of 4-isobutylphenyl-4'-methylphenyl iodonium hexafluorophosphate (manufactured by BASF, tradename: Irgacure 250) as a photopolymerization initiator, and 0.5 part by weight of the oligomer obtained by the reaction of 2-ethyl-9,10-dihydroxyanthracene and sebacoyl chloride obtained in Example 5 as a photocationic polymerization sensitizer, were mixed at room temperature to prepare a photocationic polymerizable composition. The photopolymerizable composition was subjected to photo DSC measurement, whereupon the total heating value in one minute from initiation of light irradiation was 94 mJ/mg.

Photo-Curing Rate Evaluation Example 2

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and isophorone diisocyanate obtained in the same manner as in Example 6, whereupon the total heating value in one minute from initiation of light irradiation was 52 mJ/mg.

Photo-Curing Rate Evaluation Example 3

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and 1,5-dibromopentane obtained in the same manner as in Example 10, whereupon the total heating value in one minute from initiation of light irradiation was 102 mJ/mg.

[Photo-Curing Rate Evaluation Example 4]

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and 1,9-dibromononane obtained in the same manner as in Example 12, whereupon the total heating value in one minute from initiation of light irradiation was 134 mJ/mg.

Photo-Curing Rate Evaluation Example 5

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and 1,10-dibromodecane obtained in the same manner as in Example 13, whereupon the total heating value in one minute from initiation of light irradiation was 142 mJ/mg.

Photo-Curing Rate Evaluation Example 6

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and 1,5-dibromo-3-methylpentane obtained in the same manner as in Example 14, whereupon the total heating value in one minute from initiation of light irradiation was 186 mJ/mg.

Photo-Curing Rate Evaluation Example 7

The photo DSC measurement was conducted in the same manner as in [Photo-curing rate Evaluation Example 1] except that the oligomer obtained by the reaction of 2-ethyl-9,10-dihydroxyanthracene and sebacoyl chloride in [Photo-curing rate Evaluation Example 1] was changed to the oligomer obtained by the reaction of 9,10-dihydroxyanthracene and neopentyl glycol diglycidyl ether obtained in the same manner as in Example 15, whereupon the total heating value in one minute from initiation of light irradiation was 114 mJ/mg.

Photo-Curing Rate Comparative Example 1

100 Parts by weight of 3',4'-epoxycyclohexylmethyl-3,4-epoxycyclohexane carboxylate (manufactured by Daicel Corporation, tradename: CELLOXIDE 2021P, registered trademark) as a photocationic polymerizable compound and 2 parts by weight of 4-isobutylphenyl-4'-methylphenyl iodonium hexafluorophosphate (manufactured by BASF, tradename: Irgacure 250) as a photopolymerization initiator were mixed at room temperature to prepare a photocationic polymerizable composition. The photopolymerizable composition was subjected to photo DSC measurement, whereupon the total heating value in one minute from initiation of light irradiation was 0.3 mJ/mg.

Photo-Curing Rate Comparative Example 2

The photo DSC measurement was conducted in the same manner as in [Photo-curing rate Evaluation Example 1] except that 9,10-dibutoxyanthracene as a known photopolymerization sensitize was used instead of the oligomer obtained by the reaction of 2-ethyl-9,10-dihydroxyanthracene and sebacoyl chloride in [Photo-curing rate Evaluation Example 1], whereupon the total heating value in one minute from initiation of light irradiation was 147 mJ/mg.

The results of Photo-curing rate Evaluation Examples 1 to 7 and Comparative Examples 1 and 2 are shown in Table 9.

TABLE 9

| Photo-curing rate Evaluation Examples | Photopolymerization sensitizer compound structural formula | Heating value (mJ/mg) |
|---|---|---|
| Evaluation Example 1 | (2-25) | 94 |
| Evaluation Example 2 | (3-6) | 52 |
| Evaluation Example 3 | (4-6) | 102 |
| Evaluation Example 4 | (4-11) | 134 |

TABLE 9-continued

| Photo-curing rate Evaluation Examples | Photopolymerization sensitizer compound structural formula | Heating value (mJ/mg) |
|---|---|---|
| Evaluation Example 5 | (4-12) | 142 |
| Evaluation Example 6 | (4-8) | 186 |
| Evaluation Example 7 | (5-2) | 114 |
| Comparative Example 1 | Nil | 0.3 |
| Comparative Example 2 | | 147 |

The photopolymerizability evaluation test for a radical polymerizable composition employing the compound of the present invention as a photoradical polymerization sensitizer will be described below.

Photo-Curing Rate Evaluation Example 8

25 Parts by weight of trimethylolpropane triacrylate (manufactured by Tokyo Chemical Industry Co., Ltd.) and 75 parts by weight of phenoxyethyl methacrylate (manufactured by Hitachi Chemical Company, Ltd. as photoradical polymerizable compounds, and 4 parts by weight of 4-isobutylphenyl-4'-methylphenyl iodonium hexafluorophosphate (manufactured by BASF, tradename: Irgacure 250) as a photoinitiator and 0.5 part by weight of the oligomer obtained by the reaction of 9,10-dihydroxyanthracene and isophorone diisocyanate obtained in Example 6 as a photocationic polymerization sensitizer were mixed to prepare a photoradical polymerizable composition. The photopolymerizable composition was subjected to photo DSC measurement, whereupon the total heating value in one minute from initiation of light irradiation was 75 mJ/mg.

Photo-Curing Rate Evaluation Example 9

The photo DSC measurement was conducted in the same manner as in [Photo-curing rate Evaluation Example 8] except that the oligomer obtained by the reaction of 9,10-dihydroxyanthracene and isophorone diisocyanate in [Photo-curing rate Evaluation Example 8] was changed to the oligomer obtained by the reaction of 9,10-dihydroxyanthracene and 1,5-dibromopentane obtained in the same manner as in Example 10, whereupon the total heating value in one minute from initiation of light irradiation was 258 mJ/mg.

Photo-Curing Rate Evaluation Example 10

The photo DSC measurement was conducted in the same manner as in [Photo-curing rate Evaluation Example 8] except that the oligomer obtained by the reaction of 9,10-dihydroxyanthracene and isophorone diisocyanate in [Photo-curing rate Evaluation Example 8] was changed to the oligomer obtained by the reaction of 9,10-dihydroxyanthracene and 1,9-dibromononane obtained in the same manner as in Example 12, whereupon the total heating value in one minute from initiation of light irradiation was 51 mJ/mg.

Photo-Curing Rate Evaluation Example 11

The photo DSC measurement was conducted in the same manner as in [Photo-curing rate Evaluation Example 8] except that the oligomer obtained by the reaction of 9,10-dihydroxyanthracene and isophorone diisocyanate in [Photo-curing rate Evaluation Example 8] was changed to the oligomer obtained by the reaction of 9,10-dihydroxyanthracene and 1,10-dibromodecane obtained in the same manner as in Example 13, whereupon the total heating value in one minute from initiation of light irradiation was 58 mJ/mg.

Photo-Curing Rate Evaluation Example 12

The photo DSC measurement was conducted in the same manner as in [Photo-curing rate Evaluation Example 8] except that the oligomer obtained by the reaction of 9,10-dihydroxyanthracene and isophorone diisocyanate in [Photo-curing rate Evaluation Example 8] was changed to the oligomer obtained by the reaction of 9,10-dihydroxyanthracene and 1,5-dibromo-3-methylpentane obtained in the same manner as in Example 14, whereupon the total heating value in one minute from initiation of light irradiation was 56 mJ/mg.

Photo-Curing Rate Evaluation Example 13

The photo DSC measurement was conducted in the same manner as in [Photo-curing rate Evaluation Example 8] except that the oligomer obtained by the reaction of 9,10-dihydroxyanthracene and isophorone diisocyanate in [Photo-curing rate Evaluation Example 8] was changed to the oligomer obtained by the reaction of 9,10-dihydroxyanthracene and neopentyl glycol diglycidyl ether obtained in the same manner as in Example 15, whereupon the total heating value in one minute from initiation of light irradiation was 164 mJ/mg.

Photo-Curing Rate Comparative Example 3

25 Parts by weight of timethylolpropane triacrylate (manufactured by Tokyo Chemical Industry Co., Ltd.) and 75 parts by weight of phenoxyethyl methacrylate (manufactured by Hitachi Chemical Company, Ltd.) as photoradical polymerizable compounds, and 4 parts by weight of 4-isobutylphenyl-4'-methylphenyl iodonium hexafluorophosphate (manufactured by BASF, tradename: Irgacure 250) as a photoinitiator were mixed at room temperature to prepare a photoradical polymerizable composition. The photopolymerizable composition was subjected to the photo DSC measurement, whereupon the total heating value in one minute from initiation of light irradiation was 3 mJ/mg.

Photo-Curing Rate Comparative Example 4

The photo DSC measurement was conducted in the same manner as in [Photo-curing rate Evaluation Example 8] except that 9,10-dibutoxyoanthracene as a known photopolymerization sensitizer was used instead of the oligomer obtained by the reaction of 9,10-dihydroxyanthracene and isophorone diisocyanate in [Photo-curing rate Evaluation Example 8], whereupon the total heating value in one minute from initiation of light irradiation was 15 mJ/mg.

The results of Photo-curing rage Evaluation Examples 8 to 13 and Comparative Examples 3 and 4 are shown in Table 10.

TABLE 10
| Photo-curing rate Evaluation Examples | Photopolymerization sensitizer compound structural formula | Heating value (mJ/mg) |
|---|---|---|
| Evaluation Example 8 | 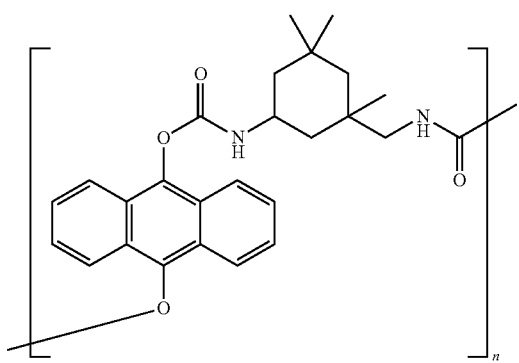<br>(3-6) | 75 |
| Evaluation Example 9 | 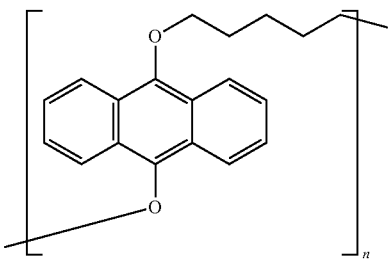<br>(4-6) | 258 |
| Evaluation Example 10 | 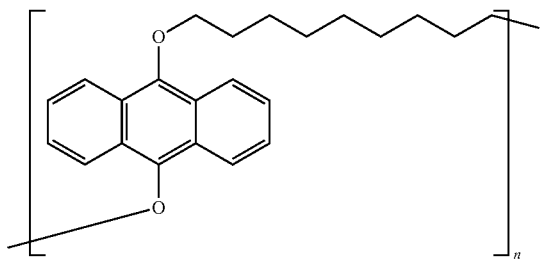<br>(4-11) | 51 |
| Evaluation Example 11 | 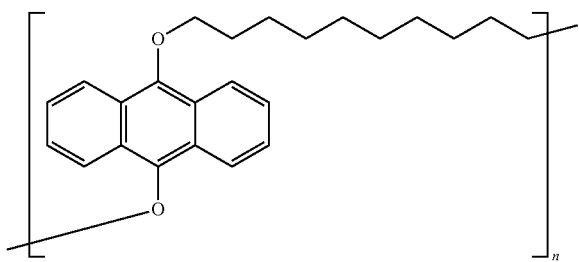<br>(4-12) | 58 |

TABLE 10-continued

| Photo-curing rate Evaluation Examples | Photopolymerization sensitizer compound structural formula | Heating value (mJ/mg) |
|---|---|---|
| Evaluation Example 12 | (4-8) | 56 |
| Evaluation Example 13 | (5-2) | 164 |
| Comparative Example 3 | Nil | 3 |
| Comparative Example 4 | (9,10-dibutoxyanthracene structure) | 15 |

As evident from comparison of the results in Photo-curing rate Evaluation Examples 1 to 7 and Photo-curing rate Comparative Example 1, by using the oligomer of a 9,10-bis(substituted oxy)anthracene compound of the present invention for photocationic polymerization, the total heating value is increased and the polymerization reaction is remarkably promoted. Further, as evident from comparison of the results of Photo-curing rate Evaluation Examples 8 to 13 and Photo-curing rate Comparative Example 1, by using the oligomer of a 9,10-bis(substituted oxy)anthracene compound of the present invention also in photoradical polymerization, the total heating value is increased, and the polymerization reaction is remarkably promoted. That is, it is found that the oligomer of a 9,10-bis(substituted oxy)anthracene compound of the present invention has a photopolymerization sensitizing effect both for photocationic polymerization and photoradical polymerization.

Further, as evident from comparison of the results in Photo-curing rate Evaluation Examples 1 to 8 and Photo-curing rate Comparative Example 2, the oligomer of a 9,10-bis(substituted oxy)anthracene compound of the present invention has a photopolymerization sensitizing effect equal to or higher than that of 9,10-dibutoxyanthracene which is a known photopolymerization sensitizer in photocationic polymerization. Further, as evident from comparison of the results in Photo-curing rate Evaluation Examples 8 to 13 and Photo-curing rate Comparative Example 4, the oligomer of a 9,10-bis(substituted oxy)anthracene compound of the present invention has a photopolymerization sensitizing effect equal to or higher than that of the 9,10-dibutoxyanthracene which is a known photopolymerization sensitizer also in photoradical polymerization.

(Examples for Evaluation of Migration Resistance in Photocationic Polymerization)

Migration Evaluation Example 1

100 Parts of 3',4'-epoxycyclohexylmethyl-3,4-epoxycyclohexanecarboxylate (manufactured by Daicel Corporation, tradename: CELLOXIDE 2021P, registered trademark)

as an epoxy photocationic polymerizable compound, and 0.5 g of the oligomer obtained by the reaction of 2-ethyl-9,10-dihydroxyanthracene and sebacoyl chloride prepared in the method in Example 5 as a photocationic polymerization sensitizer were mixed to prepare a composition, which was applied on a polyester film to a film thickness of 12 micron by a bar coater. The obtained coated film was covered with a low density polyethylene film (film thickness: 30 micron) and stored in a dark place for one day, for three days or for six days, and after storage, each polyethylene film was peeled, washed with acetone and dried, and then the UV spectrum of the film was measured and the absorbance at 260 nm was measured. The absorbance resulting from the oligomer obtained by the reaction of 2-ethyl-9,10-dihydroxyanthracene and sebacoyl chloride was calculated as 9,10-dibutoxyanthracene. The absorbance was 0.011 after storage for one day, 0.005 after storage for three days, and 0.004 after storage for six days.

Migration Evaluation Example 2

The test was carried out in the same manner as in Migration Evaluation Example 1 except that the oligomer obtained by the reaction of 9,10-dihydroxyanthracene and isophorone diisocyanate prepared by the method in the same manner as in Example 6 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and isophorone diisocyanate as calculated as 9,10-dibutoxyanthracene was 0.000 after storage for one day, after storage for three days and after storage for six days.

Migration Evaluation Example 3

The test was carried out in the same manner as in Migration Evaluation Example 1 except that the oligomer obtained by the reaction of 9,10-dihydroxyanthracene and 1,5-dibromopentane prepared by the method in the same manner as in Example 10 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and 1,5-dibromopentane as calculated as 9,10-dibutoxyanthracene was 0.003 after storage for one day, 0.000 after storage for three days and 0.000 after storage for six days.

Migration Evaluation Example 4

The test was carried out in the same manner as in Migration Evaluation Example 1 except that the oligomer obtained by the reaction of 9,10-dihydroxyanthracene and 1,9-dibromononane prepared by the method in the same manner as in Example 12 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and 1,9-dibromononane as calculated as 9,10-dibutoxyanthracene was 0.007 after storage for one day, 0.009 after storage for three days and 0.004 after storage for six days.

Migration Evaluation Example 5

The test was carried out in the same manner as in Migration Evaluation Example 1 except that the oligomer obtained by the reaction of 9,10-dihydroxyanthracene and 1,10-dibromodecane prepared by the method in the same manner as in Example 13 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and 1,10-dibromodecane as calculated as 9,10-dibutoxyanthracene was 0.014 after storage for one day, 0.020 after storage for three days and 0.043 after storage for six days.

Migration Evaluation Example 6

The test was carried out in the same manner as in Migration Evaluation Example 1 except that the oligomer obtained by the reaction of 9,10-dihydroxyanthracene and 1,5-dibromo-3-methylpentane prepared by the method in the same manner as in Example 14 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and 1,5-dibromo-3-methylpentane as calculated as 9,10-dibutoxyanthracene was 0.000 after storage for one day, 0.000 after storage for three days and 0.001 after storage for six days.

Migration Evaluation Example 7

The test was carried out in the same manner as in Migration Evaluation Example 1 except that the oligomer obtained by the reaction of 9,10-dihydroxyanthracene and neopentyl glycol diglycidyl ether prepared by the method in the same manner as in Example 15 was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance resulting from the oligomer obtained by the reaction of 9,10-dihydroxyanthracene and neopentyl glycol diglycidyl ether as calculated as 9,10-dibutoxyanthracene was 0.002 after storage for one day, 0.000 after storage for three days and 0.000 after storage for six days.

Migration Comparative Example 1

The test was carried out in the same manner as in Evaluation Example 1 except that 9,10-dibutoxyanthracene as a known photocationic polymerization sensitizer was used instead of the oligomer obtained by the reaction of 2-ethyl-9,10-dihydroxyanthracene and sebacoyl chloride as the photopolymerization sensitizer. The absorbance at 260 nm of the polyethylene film washed with acetone was measured and as a result, the absorbance of 9,10-dibutoxyanthracene was 0.430 after storage for one day, 0.452 after storage for two days and 0.427 after storage for four days.

The results of Migration Evaluation Examples 1 to 7 and Comparative Example 1 are shown in Table 11.

TABLE 11

| Migration Evaluation Examples | Photopolymerization sensitizer compound structural formula | Absorbance After storage for one day | After storage for three days | After storage for six days |
|---|---|---|---|---|
| Evaluation Example 1 | (2-25) | 0.011 | 0.005 | 0.004 |
| Evaluation Example 2 | (3-6) | 0.000 | 0.000 | 0.000 |
| Evaluation Example 3 | (4-6) | 0.003 | 0.000 | 0.000 |
| Evaluation Example 4 | (4-11) | 0.007 | 0.009 | 0.004 |

TABLE 11-continued
| Migration Evaluation Examples | Photopolymerization sensitizer compound structural formula | Absorbance After storage for one day | After storage for three days | After storage for six days |
|---|---|---|---|---|
| Evaluation Example 5 | 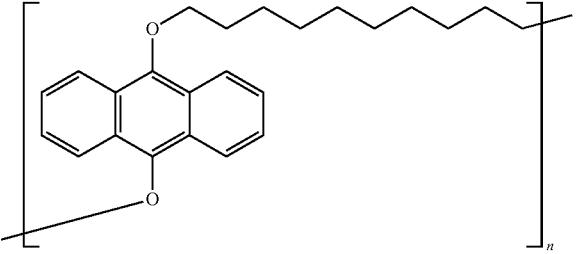 (4-12) | 0.014 | 0.020 | 0.043 |
| Evaluation Example 6 | 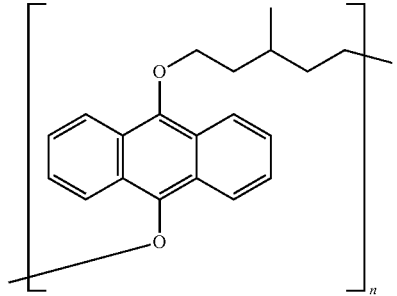 (4-8) | 0.000 | 0.000 | 0.001 |
| Evaluation Example 7 | 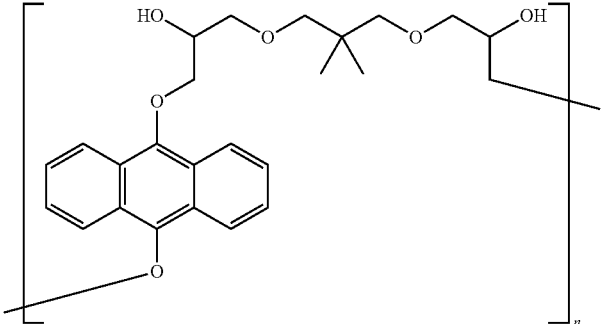 (5-2) | 0.002 | 0.000 | 0.000 |
| Comparative Example 1 | 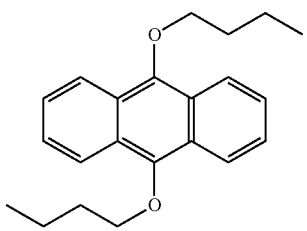 | 0.430 | 0.452 | 0.427 |

(Examples for Evaluation of Migration Resistance in Photoradical Polymerization)

Migration Evaluation Example 8

25 Parts of trimethylolpropane triacrylate and 75 parts of phenoxyethyl methacrylate as photoradical polymerizable compounds, and 0.5 part of the oligomer obtained by the reaction of 9,10-dihydroxyanthracene and isophorone diisocyanate prepared by the method in the same manner as in Example 6 as a photoradical polymerization sensitizer, were mixed to prepare a composition, which was applied on a polyester film to a film thickness of 12 micron by a bar coater. Then, the obtained coated film was covered with a low density polyethylene film (film thickness: 30 micron) and stored in a dark place for one day, for three days or for six days, and after storage, each covering polyethylene film was peeled, washed with acetone and dried, and the UV spectrum of the polyethylene film was measured, and the absorbance at 260 nm was measured. The absorbance resulting from the oligomer obtained by the reaction of 9,10-dihydroxyanthracene and isophorone diisocyanate as calculated as 9,10-dibutoxyanthracene was 0.000 after storage for one day, after storage for three days and after storage for six days.

Migration Evaluation Example 9

The test was carried out in the same manner as in Migration Evaluation Example 8 except that the oligomer obtained by the reaction of 9,10-dihydroxyanthracene and 1,5-dibromopentane prepared by the method in the same manner as in Example 10 was used instead of the oligomer obtained by the reaction of 9,10-dihydroxyanthracene and isophorone diisocyanate. The absorbance at 260 nm of the polyethylene film washed with acetone was measured and as a result, the absorbance resulting from the oligomer obtained by the reaction of 9,10-dihydroxyanthracene and 1,5-dibromopentane as calculated as 9,10-dibutoxyanthracene was 0.012 after storage for one day, 0.012 after storage for three days and 0.012 after storage for six days.

Migration Evaluation Example 10

The test was carried out in the same manner as in Migration Evaluation Example 8 except that the oligomer obtained by the reaction of 9,10-dihydroxyanthracene and 1,9-dibromononane prepared by the method in the same manner as in Example 12 was used instead of the oligomer obtained by the reaction of 9,10-dihydroxyanthracene and isophorone diisocyanate. The absorbance at 260 nm of the polyethylene film washed with acetone was measured and as a result, the absorbance resulting from the oligomer obtained by the reaction of 9,10-dihydroxyanthracene and 1,9-dibromononane as calculated as 9,10-dibutoxyanthracene was 0.006 after storage for one day, 0.009 after storage for three days and 0.008 after storage for six days.

Migration Evaluation Example 11

The test was carried out in the same manner as in Migration Evaluation Example 8 except that the oligomer obtained by the reaction of 9,10-dihydroxyanthracene and 1,10-dibromodecane prepared by the method in the same manner as in Example 13 was used instead of the oligomer obtained by the reaction of 9,10-dihydroxyanthracene and isophorone diisocyanate. The absorbance at 260 nm of the polyethylene film washed with acetone was measured and as a result, the absorbance resulting from the oligomer obtained by the reaction of 9,10-dihydroxyanthracene and 1,10-dibromodecane as calculated as 9,10-dibutoxyanthracene was 0.015 after storage for one day, 0.035 after storage for three days and 0.013 after storage for six days.

Migration Evaluation Example 12

The test was carried out in the same manner as in Migration Evaluation Example 8 except that the oligomer obtained by the reaction of 9,10-dihydroxyanthracene and 1,5-dibromo-3-methylpentane prepared by the method in the same manner as in Example 14 was used instead of the oligomer obtained by the reaction of 9,10-dihydroxyanthracene and isophorone diisocyanate. The absorbance at 260 nm of the polyethylene film washed with acetone was measured and as a result, the absorbance resulting from the oligomer obtained by the reaction of 9,10-dihydroxyanthracene and 1,5-dibromo-3-methylpentane as calculated as 9,10-dibutoxyanthracene was 0.000 after storage for one day, 0.004 after storage for three days and 0.000 after storage for six days.

Migration Evaluation Example 13

The test was carried out in the same manner as in Migration Evaluation Example 8 except that the oligomer obtained by the reaction of 9,10-dihydroxyanthracene and neopentyl glycol diglycidyl ether prepared by the method in the same manner as in Example 15 was used instead of the oligomer obtained by the reaction of 9,10-dihydroxyanthracene and isophorone diisocyanate. The absorbance at 260 nm of the polyethylene film washed with acetone was measured and as a result, the absorbance resulting from the oligomer obtained by the reaction of 9,10-dihydroxyanthracene and neopentyl glycol diglycidyl ether as calculated as 9,10-dibutoxyanthracene was 0.000 after storage for one day, after storage for three days and after storage for six days.

Migration Comparative Example 2

The test was carried out in the same manner as in Migration Evaluation Example 1 except that 9,10-dibutoxyanthracene as a known photoradical polymerization sensitizer was used instead of the oligomer obtained by the reaction of 9,10-dihydroxyanthracene and isophorone diisocyanate. The absorbance at 260 nm of the polyethylene film washed with acetone was measured and as a result, the absorbance of 9,10-dibutoxyanthracene as 0.402 after storage for one day, 0.401 after storage for three days and 0.409 after storage for six days.

The results of Migration Evaluation Examples 8 to 13 and Comparative Example 2 are shown in Table 12.

TABLE 12

| Migration Evaluation Examples | Photopolymerization sensitizer compound structural formula | Absorbance | | |
|---|---|---|---|---|
| | | After storage for one day | After storage for three days | After storage for six days |
| Evaluation Example 8 | (3-6) | 0.000 | 0.000 | 0.000 |
| Evaluation Example 9 | (4-6) | 0.012 | 0.012 | 0.012 |
| Evaluation Example 10 | (4-11) | 0.006 | 0.009 | 0.008 |
| Evaluation Example 11 | (4-12) | 0.015 | 0.035 | 0.013 |

TABLE 12-continued

| Migration Evaluation Examples | Photopolymerization sensitizer compound structural formula | Absorbance | | |
|---|---|---|---|---|
| | | After storage for one day | After storage for three days | After storage for six days |
| Evaluation Example 12 | 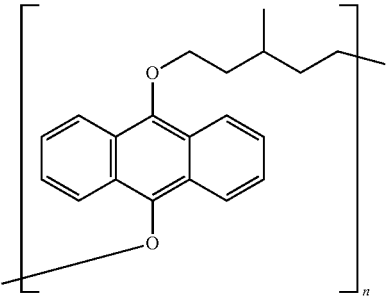<br>(4-8) | 0.000 | 0.004 | 0.000 |
| Evaluation Example 13 | 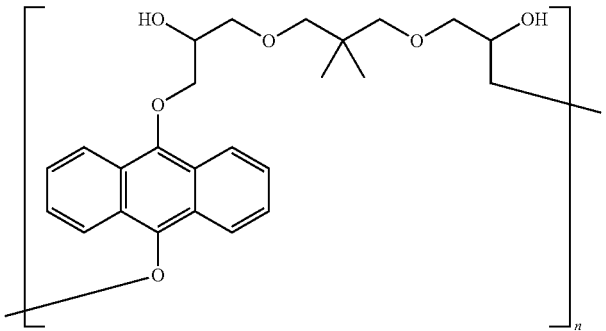<br>(5-2) | 0.000 | 0.000 | 0.000 |
| Comparative Example 2 | 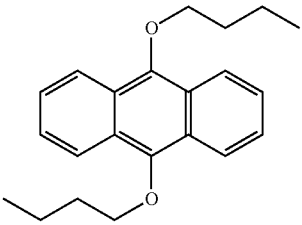 [SMILES: CCCCOc1c2ccccc2c(OCCCC)c2ccccc12] | 0.402 | 0.401 | 0.409 |

As evident from comparison of Migration Evaluation Examples 1 to 7 and Migration Comparative Example 1, in the photocationic polymerizable composition, 9,10-dibutoxyanthracene which is a known photocationic polymerization sensitizer migrates to the film covering the photocationic polymerizable composition to a considerable extent, whereas the degree of migration of the oligomer of a 9,10-bis(substituted oxy)anthracene compound of the present invention is very low in each Example, and the oligomer of the present invention is considered to be excellent in the migration resistance. Further, as evident from comparison of Migration Evaluation Examples 8 to 13 and Migration Comparative Example 2, in the photoradical polymerizable composition also, 9,10-dibutoxyanthracene which is a known photoradical polymerization sensitizer migrates to the film covering the photoradical polymerizable composition to a considerable extent, whereas the degree of migration of the oligomer of a 9,10-bis(substituted oxy)anthracene compound of the present invention is very low in each Example, and the oligomer of the present invention is considered to be excellent in the migration resistance.

From the above results, it is found that the oligomer of a 9,10-bis(substituted oxy)anthracene compound of the present invention is, in photocationic polymerization and photoradical polymerization, a compound not only having a photopolymerization sensitizing effect equal to a 9,10-dibutoxyanthracene compound which is a known photopolymerization sensitizer but also having high migration resistance, and is a compound very useful as a photopolymerization sensitizer.

INDUSTRIAL APPLICABILITY

The oligomer of a 9,10-bis(substituted oxy)anthracene compound of the present invention is, in photocationic polymerization and photoradical polymerization, a photopolymerizable sensitizer not only useful as a photopolymerization sensitizer but also having high migration resistance in a cured product of the photopolymerizable composition, and practically very useful in applications in which migration is problematic, such as for adhesive application.

The invention claimed is:

1. A photopolymerization sensitizer, comprising:
an oligomer of a 9,10-bis(substituted oxy)anthracene compound having repeating units of formula (3):

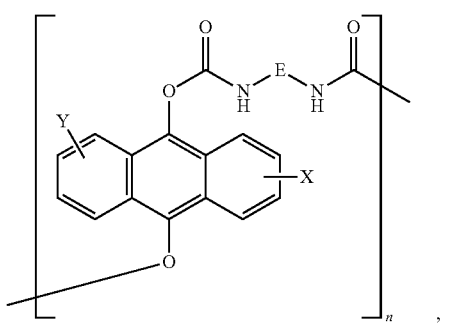

(3)

wherein n is a repetition number in a range of from 2 to 50,
X and Y are independently H, a $C_{1-8}$ alkyl group, or a halogen atom,
E is a $C_{1-20}$ alkylene group or a $C_{6-20}$ arylene group, the alkylene group optionally comprising an O, N, S, a benzene ring, or a naphthalene ring, the benzene ring and the naphthalene ring being optionally substituted by an alkyl group, the arylene group optionally having a substituent, and a plurality of rings being optionally bonded by an alkylene group, O, N, or S.

2. A photopolymerization initiator composition, comprising:
a photopolymerization initiator; and
a photopolymerization sensitizer comprising an oligomer of a 9,10-bis(substituted oxy)anthracene compound having repeating units of formula (3) or an oligomer of a 9,10-bis(substituted oxy)anthracene compound having repeating units of formula (5):

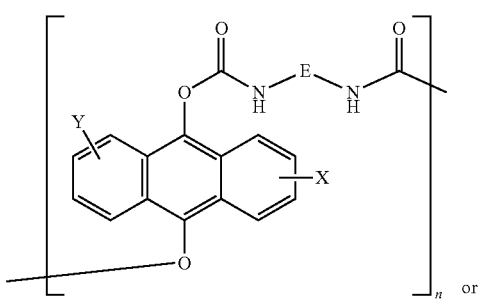

(3)

or

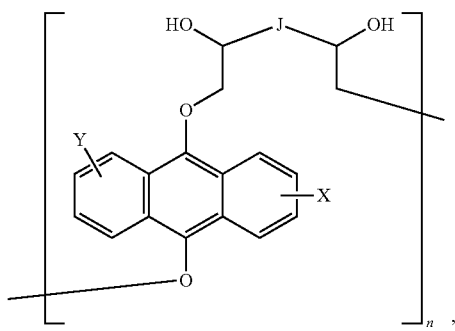

(5)

wherein
n is a repetition number in a range of from 2 to 50,
X and Y are independently H, a $C_{1-8}$ alkyl group, or a halogen atom, and
E and J are independently a $C_{1-20}$ alkylene group or a $C_{6-20}$ arylene group, the alkylene group optionally comprising an O, N, S, a benzene ring, or a naphthalene ring, the benzene ring and the naphthalene ring being optionally substituted by an alkyl group, the arylene group optionally having a substituent, and a plurality of rings being optionally bonded by an alkylene group, O, N, or S.

3. A photopolymerizable composition, comprising:
the photopolymerization initiator composition of claim 2; and
a photocationic polymerizable compound.

4. A photopolymerizable composition, comprising:
the photopolymerization initiator composition of claim 2; and
a photoradical polymerizable compound.

5. A photopolymerization sensitizer, comprising:
an oligomer of a 9,10-bis(substituted oxy)anthracene compound having repeating units of formula (5):

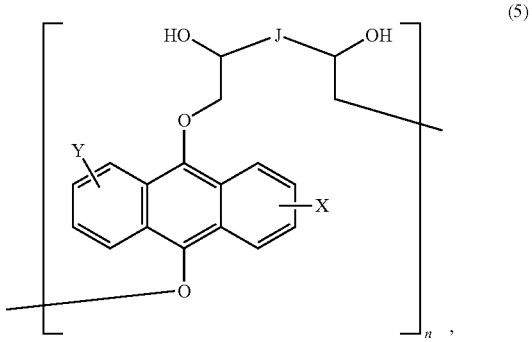

(5)

wherein
n is a repetition number in a range of from 2 to 50,
X and Y are independently H, a $C_{1-8}$ alkyl group, or a halogen atom,
J is a $C_{1-20}$ alkylene group or a $C_{6-20}$ arylene group, the alkylene group optionally comprising an O, N, S, benzene ring, or naphthalene ring, the benzene ring and the naphthalene ring being optionally substituted by an alkyl group, the arylene group optionally having a substituent, and a plurality of rings being optionally bonded by an alkylene group, O, N, or S.

* * * * *